(12) United States Patent
Margon

(10) Patent No.: US 8,994,536 B2
(45) Date of Patent: Mar. 31, 2015

(54) WIRELESS PHYSIOLOGY MONITOR

(75) Inventor: Kenneth Margon, Selangor (MY)

(73) Assignee: Xanthia Global Limited (VG)

( * ) Notice: Subject to any disclaimer, the term of this patent is extended or adjusted under 35 U.S.C. 154(b) by 0 days.

(21) Appl. No.: 13/247,999

(22) Filed: Sep. 28, 2011

(65) Prior Publication Data

US 2012/0146796 A1      Jun. 14, 2012

Related U.S. Application Data

(63) Continuation-in-part of application No. 12/712,488, filed on Feb. 25, 2010, and a continuation-in-part of application No. PCT/US2010/025325, filed on Feb. 25, 2010.

(60) Provisional application No. 61/155,510, filed on Feb. 25, 2009, provisional application No. 61/179,605, filed on May 19, 2009.

(51) Int. Cl.

| | |
|---|---|
| *G08B 23/00* | (2006.01) |
| *G08B 13/18* | (2006.01) |
| *A61B 5/00* | (2006.01) |
| *A61B 5/08* | (2006.01) |
| *A61B 5/02* | (2006.01) |
| *A61B 5/04* | (2006.01) |
| *G01S 13/56* | (2006.01) |

(Continued)

(52) U.S. Cl.
CPC . *G01S 13/56* (2013.01); *A61B 5/05* (2013.01); *A61B 5/11* (2013.01); *G01S 7/003* (2013.01); *A61B 5/024* (2013.01); *A61B 5/0816* (2013.01); *A61B 5/1107* (2013.01); *A61B 5/1117* (2013.01); *A61B 5/113* (2013.01); *A61B 5/117* (2013.01); *A61B 5/7207* (2013.01); *A61B 5/725* (2013.01); *A61B 2562/0219* (2013.01); *A61B 5/6891* (2013.01)
USPC ............ 340/573.1; 340/573.5; 340/554; 340/572.4; 600/300; 600/529; 600/508; 600/519

(58) Field of Classification Search
CPC .................................................. A61B 5/0205
USPC ............................................ 340/573.1, 572.4
See application file for complete search history.

(56) References Cited

U.S. PATENT DOCUMENTS

| | | | | |
|---|---|---|---|---|
| 5,458,123 | A | * | 10/1995 | Unger ..................... 600/509 |
| 6,740,033 | B1 | * | 5/2004 | Olejniczak et al. .......... 600/301 |

(Continued)

*Primary Examiner* — Jennifer Mehmood
*Assistant Examiner* — Pameshanand Mahase
(74) *Attorney, Agent, or Firm* — San Diego IP Law Group LLP

(57) ABSTRACT

The present invention provides a new non-invasive technique for organ, e.g., heart and lung, monitoring. In at least one embodiment of the invention, a subject is radiated with a non-harmful and relatively low power electromagnetic source diagnostic signal normally associated with a communications protocol such as, but not limited to a version of the IEEE 802.11(x) family of protocols in the 2.4, 3.6, or 5 GHz spectrum bands. After passing through the patient, a return signal is acquired from the patient and compared to the original source signal. The differences between the source and modified signals are then analyzed to monitor the heart, e.g., measure heart rate and detect defects within the heart, and the lung. For example, using Doppler Effect principles, heart rate and motion can be measured from the differences in frequency, phase, and/or wavelength between the source signal and the modified signal reflected back from the heart moving within the patient.

15 Claims, 14 Drawing Sheets

(51) Int. Cl.
  *A61B 5/05* (2006.01)
  *A61B 5/11* (2006.01)
  *G01S 7/00* (2006.01)
  *A61B 5/024* (2006.01)
  *A61B 5/113* (2006.01)
  *A61B 5/117* (2006.01)

(56) References Cited

U.S. PATENT DOCUMENTS

| | | | |
|---|---|---|---|
| 7,399,277 B2 * | 7/2008 | Saidara et al. | 600/300 |
| 2002/0055913 A1 | 5/2002 | Rajan | |
| 2002/0065466 A1 | 5/2002 | Rather et al. | |
| 2002/0067269 A1 * | 6/2002 | Cadell et al. | 340/573.1 |
| 2002/0109600 A1 | 8/2002 | Mault et al. | |
| 2007/0043597 A1 | 2/2007 | Donaldson | |
| 2007/0063850 A1 | 3/2007 | Devaul et al. | |
| 2007/0096927 A1 * | 5/2007 | Albert | 340/573.1 |
| 2007/0247316 A1 * | 10/2007 | Wildman et al. | 340/572.4 |
| 2008/0001735 A1 | 1/2008 | Tran | |
| 2008/0119716 A1 | 5/2008 | Boric-Lubecke et al. | |
| 2008/0164999 A1 | 7/2008 | Otto | |
| 2008/0166028 A1 | 7/2008 | Turek et al. | |
| 2008/0175422 A1 | 7/2008 | Kates | |
| 2010/0198083 A1 * | 8/2010 | Lin et al. | 600/484 |

* cited by examiner (a) (b)

(a) (b)

(a) (b)

(a) (b)

WIRELESS PHYSIOLOGY MONITOR

CROSS-REFERENCE TO RELATED APPLICATIONS

This continuation-in-part application claims the benefit of U.S. patent application Ser. No. 12/712,488 and PCT/US10/025325, both filed on Feb. 25, 2010, and both entitled "Wireless Physiology Monitor," which claim priority under 35 U.S.C. §119(e) to U.S. Provisional Patent Application No. 61/155,510, entitled "WiFi OFDM Modulated Carrier for Heart and Lung Monitoring," filed Feb. 25, 2009, and U.S. Provisional Patent Application No. 61/179,605, entitled "Fall Detection and Heart/Lung Monitoring," filed May 19, 2009. The disclosures of the above-noted applications are incorporated by reference herein in their entirety.

BACKGROUND OF THE INVENTION

1. Field of Invention

The present invention relates to physiological measurement techniques and biotelemetry (i.e., medical telemetry), and more particularly to a system, device, and method for heart and lung monitoring using a modulated radio frequency (RF) carrier, such as an IEEE 802.11(x) ("WiFi") orthogonal frequency-division multiplexing (OFDM) signal, as a diagnostic signal.

2. Description of Related Art

Several technologies have been developed to help doctors and medical professionals access, visualize, or learn more about a patient's internal organs without having to undertake an invasive medical procedure.

For example, an electrocardiogram (an "EKG") can be used to determine information about a patient's heart. Electrical waves generated by the heart are measured by electrodes that are placed on the skin of a patient. The voltage between the electrodes is displayed on a monitor for analysis of the patient's heart. EKGs have several disadvantages, however. The electrodes must be physically connected to the patient being monitored, which can be bothersome to the patient, for the duration of the EKG test. In addition, an EKG does not produce an image of the heart itself and is not a direct measurement of the motion of the heart. Therefore, the detected electrical characteristics are merely analogues of the heart's motion.

Computer axial tomography ("CAT" or "CT") scans can be used to generate three-dimensional (3D) images of a human body. CT scanners emit a fan-shaped x-ray beam, which passes through a patient's body before being detected by rotating source detectors. Depending on the type of tissue the x-rays pass through, the x-rays will be attenuated or will pass through unimpeded. The x-rays that pass through the body are detected and used to generate an image of the tissues exposed to the x-rays. Images of internal organs can therefore be generated. Yet, CT scanners suffer from numerous disadvantages. They are expensive, bulky and immobile, require patients to remain generally immobile for extended periods of time during the scanning, and expose patients to potentially harmful x-rays.

Magnetic resonance imaging ("MRI") scanners can be used to generate images of a human body. An MRI scanner uses magnetic fields to align the nuclear magnetization of hydrogen atoms in the body. The magnetization of these atoms is then altered to produce a magnetic field, which is detected by the scanner and used to generate an image. As with CT scanners, MRI scanners are expensive, very large and immobile, and require patients to remain relatively immobile during the procedure. Furthermore, MRI scanners cannot be used by some people with metal implants.

SUMMARY OF THE INVENTION

The present invention overcomes these and other deficiencies of the prior art by providing a Doppler based physiological monitoring technique that implements modulated radio signals, such as, but not limited to IEEE 802.11(x) modulated signals, as a diagnostic signal. The differences between the source diagnostic and the return signal (i.e., the modified signal after undergoing modification as it passes through a patient) are then analyzed to monitor essential and typical life processes, activities, and functions such as, but not limited to measuring heart rate and detecting heart defects, and respiratory rate. For example, using Doppler Effect principles, heart rate and motion can be measured from the differences in frequency, phase, and/or wavelength between the source signal and the modified signal reflected back from the heart moving within the patient.

In one embodiment, a method for physiology monitoring comprises the steps of: communicating a first modulated signal toward a subject, communicating a second modulated signal, different from the first modulated signal, wherein the first modulated signal and second modulated signal are combined to form a third modulated signal, and processing the third modulated signal to monitor a physiological function of an organ of the subject. The second modulated signal may be attributed to a Doppler effect reflected from the organ of the subject and the third modulated signal may comprise a bandwidth that is substantially double of the first and second modulated signals. Each modulated signal may comprise a signal selected from the group consisting of: a quadrature amplitude modulation with orthogonal frequency-division multiplexing signal; a IEEE 802.11 compliant signal; a Bluetooth compliant signal; a WiMax compliant signal; a CDMA signal; a GSM signal; a 3GPP LTE signal; and a combination thereof. The physiological function may be selected from the group consisting of: heart rate; respiratory or pulmonary rate; ventricular contraction; ventricular relaxation; atrial contraction; atrial relaxation; arrhythmia; and a combination thereof. The method may further comprise the step of detecting movement of the subject. The movement may comprise a fall. The method may further comprise the step of recording the monitored physiological function upon detection of the movement.

In another embodiment, a system for physiology monitoring comprises: a mixer for receiving a modulated signal from a fixed source and an altered modulated signal from a subject, wherein an output signal is generated by the mixer, a filter coupled to the mixer for receiving the output signal, and a circuitry to determine and monitor a physiological function of an organ of the subject. The output signal may comprise a bandwidth that is substantially double of the modulated signal and altered modulated signal. The modulated signal may comprise a signal selected from the group consisting of: a quadrature amplitude modulation with orthogonal frequency-division multiplexing signal; a IEEE 802.11 compliant signal; a Bluetooth compliant signal; a WiMax compliant signal; a CDMA signal; a GSM signal; a 3GPP LTE signal; and a combination thereof. The altered modulated signal may be attributed to a Doppler effect reflected from the organ of the subject. The circuitry may comprise a digital signal processing unit to measure, convert and analyze the output signal for determining and monitoring a physiological function of an organ of the subject. The fixed source may be transmitted from public broadcasting wireless stations. The filter may comprise a low pass filter or a bandpass filter.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF EMBODIMENTS

Figure 1:
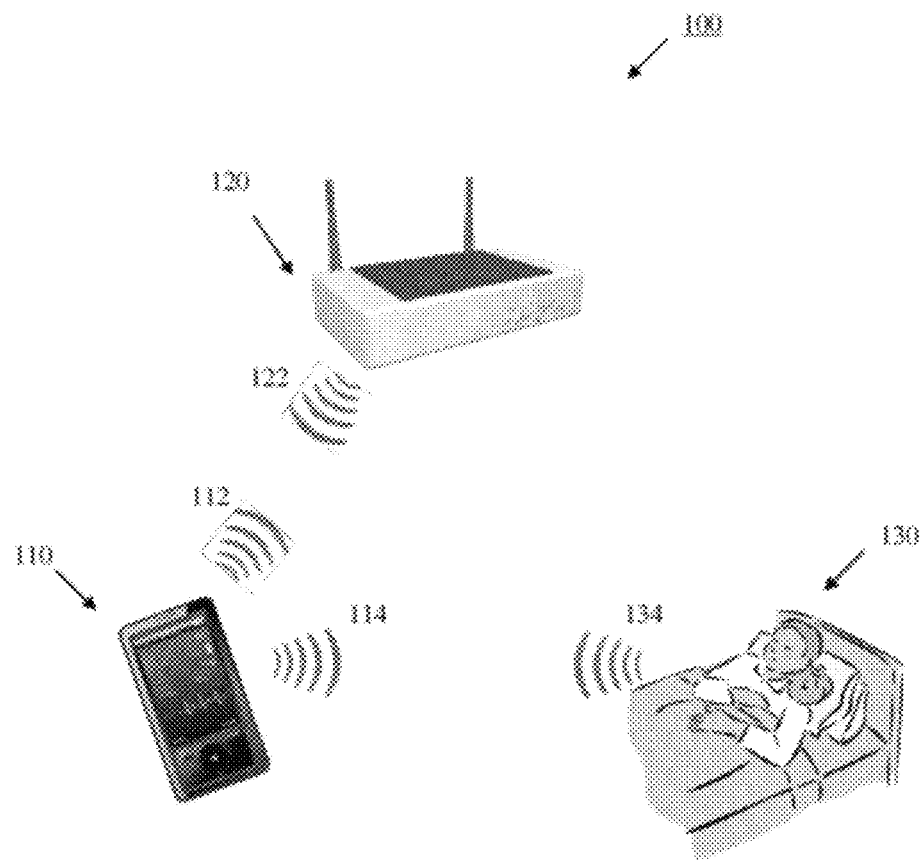
FIG. 1 illustrates a biotelemetry system according to an embodiment of the invention.

Further features and advantages of the invention, as well as the structure and operation of various embodiments of the invention, are described in detail below with reference to the accompanying FIGS. 1-24, wherein like reference numerals refer to like elements. Although the embodiments of the invention are described in the context of a radio frequency (RF) modulated carrier, such as any one of the family of IEEE 802.11(x) protocols (more commonly referred to as WiFi), one of ordinary skill in the art readily appreciates that any type of modulated communication signal can be implemented for the investigation of physiological functions within a patient. For example, the inventive concepts described herein may be implemented using any modulated or wireless communications protocol such as, but not limited to Bluetooth, WiMax (Worldwide Interoperability for Microwave Access), CDMA (Code Division Multiple Access), GSM (Global System for Mobile Communication), and 3GPP LTE (Long Term Evolution) or a signal that is generated by a pseudo-random generator and then modulated as a spread signal as in spread spectrum or Orthogonal frequency-division multiplexing ("OFDM").

The present invention provides a new non-invasive technique for physiology monitoring and assessment. In at least one embodiment of the invention, a patient is subjected to a non-harmful and relatively low power electromagnetic RF source diagnostic signal normally associated with a communications protocol such as, but not limited to a version of the IEEE 802.11(x) family of protocols in the 2.4, 3.6, or 5 GHz spectrum bands. In lay terms, that source diagnostic signal undergoes modification as it passes through the medium of the patient due to absorption, reflection, scattering, etc., the precise physics of which are readily understood by one of ordinary skill in the art. After passing through the patient, the modified signal is acquired and compared to the original source signal. The differences between the source and modified signals are then analyzed to monitor essential and typical life processes, activities, and functions such as, but not limited to measuring heart rate and detecting heart defects, and respiratory rate. For example, using Doppler Effect principles, heart rate and motion can be measured from the differences in frequency, phase, and/or wavelength between the source signal and the modified signal reflected back from the heart moving within the patient.

Although it is challenging to use a modulated carrier as the diagnostic signal because of the jittery nature of a RF mixer output, the effect of the base band signal (on the order of Megahertz) on the carrier can be considered as pseudo random noise when viewed in the low scale of heart beat frequency (on the order of hertz). To overcome this challenge, the present invention employs powerful filters to effectively eliminate this noise as detailed below.

Unlike conventional Doppler-based radar systems, which attempt to receive a signal from a quiet background, the present invention is designed to extract deviation from randomness from a background of random noise. This technique permits amplification of the received signal even though it raises the noise floor. The present invention optimizes the use of OFDM and exploits a multipath environment.

In an embodiment of the invention, the modified signal received from the patient goes through a quadrature demodulator similar to using two separate mixers. The input to the local oscillator is the original WiFi transmitted diagnostic signal (TX signal). The input to the demodulator is from the signal received back from the patient (the Doppler RX signal). The resulting output is a spectrum consisting of the error between the TX and the RX plus noise that is not related to the TX source. The TX signal is much stronger than other signals that make up the received spectrum. The Doppler radar technique of the present invention removes the strongest signal from the spectrum, which reduces the randomness of the received signal relative to the effects of the perturbations of the spectrum due to heart movement and respiration. This process also enhances the non-random characteristics that represent the perturbations to the received signal.

The fundamental concept employed in the present invention is analogous to looking for a picture in a background of static noise or finding a sign of intelligence in a sky of random radiation. The more random the noise background is the more effective the present invention is at looking for non-random changes in the received signal. Another analogy is a boat traveling across a body of water such as a lake. Whether the lake is completely calm or has a chop, the boat deforms the waves. One can say that the chop is not truly random, but looking at it from a distance it will have some visual equilibrium that is disturbed by the boat, e.g., the boat's wake. It is the disturbance in the equilibrium that the present invention is measuring—the present invention measures both the rate of change and the magnitude of the change. This allows for the detection of speed, distance, and overall size information.

In an embodiment of the invention, a functioning WiFi signal is used. The present invention measures heart rate and respiration rate using a WiFi equipped device without interfering with the normal communications and interaction between an Access Point (AP) and the WiFi device. If no AP is present, then the WiFi device is put into a 802.11 probing mode so that it transmits a signal. The IEEE 802.11 protocol signal is time-division duplex (TDD) and therefore intermittent, however it does not affect the overall measurement. The present invention processes both I and Q channels (abbreviation for respective in-phase and quadrature channels) at a bandwidth of between 10 and 11 megahertz. Because of the high bandwidth of the WiFi encoded information, it is not necessary to process the signal to account for the quadrature amplitude modulation (QAM) constellation as it is affected by the information encoded in the signal. Baseband processors typically "whiten" the data stream by limiting the number of consecutive "1s" or "0s" to prevent DC offset.

Fundamentally, the present invention looks for perturbations in a spectrum of random noise and then characterizes the perturbations. The output from the demodulator is in the form of I and Q signals—the reason for this is that since the present invention is looking for information that approaches DC, both I and Q signals are needed to maintain signal resolution near DC levels. The I and Q channels are processed by two separate analog to digital converters (ADCs) and then the spectrum is combined into input filters based on Kalman equations or other filtering algorithms such as, but not limited to modified particle filter algorithms, the implementation of which is apparent to one of ordinary skill in the art. The implementation of the Kalman equations analyzes the spectrum of input signals in both the frequency and time domains to enhance the non-random signals in the input spectrum and suppress random signal in the input spectrum.

It is clear that most of the noise in the input spectrum is not truly random. In some ways randomness is in the eye of the beholder. The appearance of randomness depends on the observer's capabilities as in the example above where a lake has a chop on it. It is really understood that the chop is driven by the wind and flows in a certain direction. At a certain height above the lake only the white caps are seen. At even a higher height all of the white caps blend into a random flat pallet. A wake of the boat moving through the waves changes the texture and color of this pallet. Kalman equations are manipulated to look for perturbation in the spectrum of frequencies input to the enhancer. The tools are mathematical and don't depend on human senses. Other filters such as an infinite impulse response (IIR) filter and/or a finite impulse response (FIR) filter could be used, but processing would require a much higher signal level. Other energy not originating from the diagnostic Wifi signal, which is technically not Doppler, also bounces off the organs and contributes to the energy evaluated by the filters. The Doppler ends up working more like a pilot signal so that the modeling can adjust dynamically and faster. The key is that the Doppler effect is used as a guide and a dynamic model of heart and lung signals is produced.

FIG. 1 illustrates a biotelemetry system 100 according to an embodiment of the invention. The system 100 comprises a device 110 (e.g., sensing device) and a network node 120, which each comprise a transmitter (not shown) and receiver (not shown) to communicate with one another through communication signals 112 and 122, which are preferably communication signals for transmission through a wireless medium, although a wired medium may be implemented as well. The network node 120 (e.g., access point) is also in communication with a network (not shown) such as, but not limited to a local network and/or the Internet. In operation, the device 110 transmits a source diagnostic signal 114 toward a patient 130. A modified signal 134 is then obtained from the movement of a targeted organ such as the heart of the patient 130 to the device 110. The device 110 includes circuitry (not shown) for measuring the differences such as, but not limited to frequency, phase, and/or wavelength differences between the source signal 114 and the modified signal 134, and for computing and displaying physiological functions such as, but not limited to heart and respiratory rate.

In an alternative embodiment of the invention, the diagnostic signal 114 may originate from background noise. For example, rather than the device 110 transmitting the source diagnostic signal 114, the diagnostic signal 114 originates from a third-party source (not shown) such as, but not limited to an access point. The device 110 detects the diagnostic signal 114 from background noise and measures the characteristics of the diagnostic signal 114 to perform the various physiological measurements noted herein. In other words, if a modulated communication signal is already present in the patient's environment, the device 110 may use such as the diagnostic signal 114 without having to transmit the diagnostic signal 114 itself.

The device 110 can take any form factor. In one embodiment of the invention, the device 110 is a standalone handheld device for optimum portability. For example, the device 110 may take the form of a pendant, which may be worn around a patient's neck. In another embodiment of the invention, the device 110 can be included as a component within a multi-purpose mobile device such as, but not limited to a cell phone, a laptop computer, a personal digital assistant (PDA) or smart-phone, e.g., Blackberry, PALM, iPhone, and the like. In yet another embodiment of the invention, the device 110 is included as a component within a relatively immobile device such as a desktop computer or wireless router such as the network node 120. Alternatively, the device 110 may be included as a part of a larger apparatus such as a hospital bed, gurney, or any type of equipment where a patient may be located or adjacent thereto. The device 110 may further include a biometric sensor (not shown) for identifying the individual using the device 110. For example, the device 110 may optionally include a fingerprint scanner, retinal scanner, or other biometric scanner, the identification and implementation of which is apparent to one of ordinary skill in the art.

Figure 2:
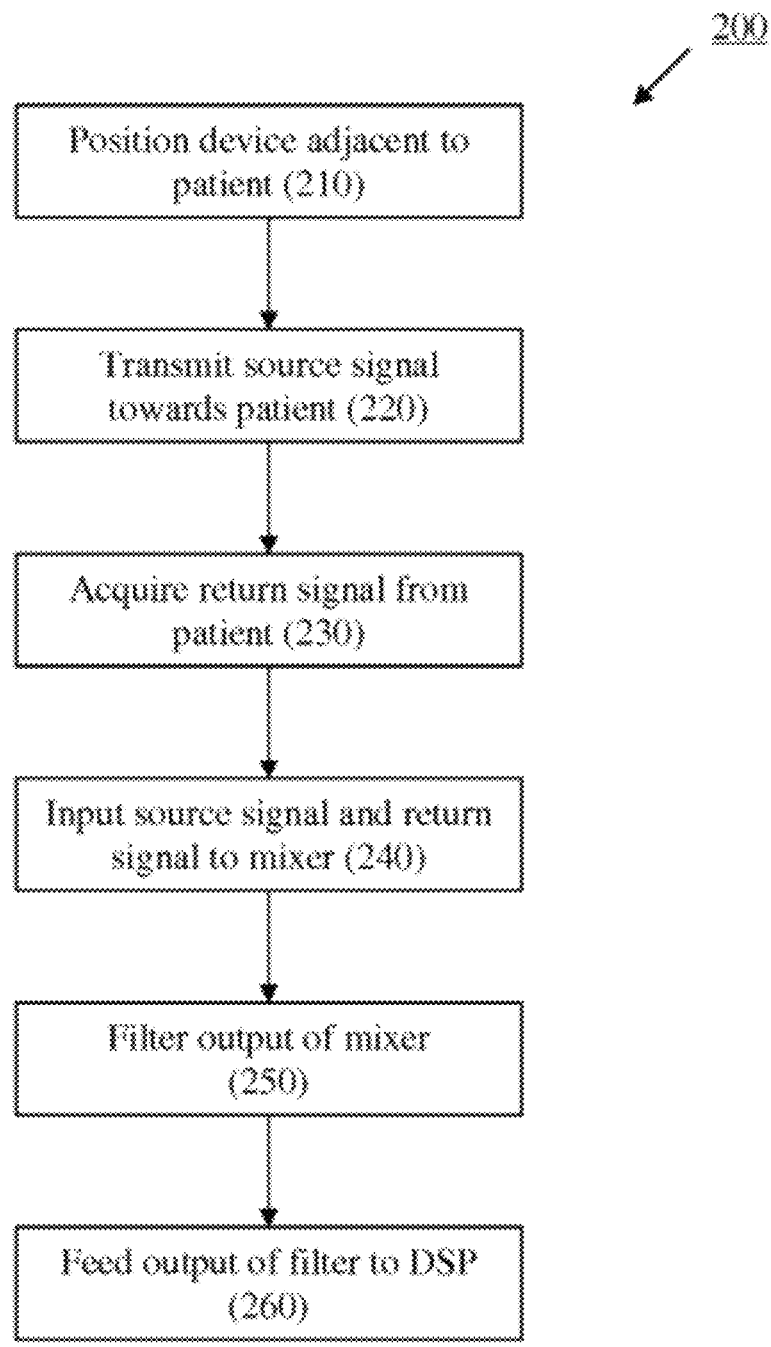
FIG. 2 illustrates a physiological measurement process according to an embodiment of the invention.

FIG. 2 illustrates a physiological measurement process 200 according to an embodiment of the invention. The device 110 is positioned (step 210) adjacent to an organ of the patient 130. The diagnostic signal 114 is then transmitted (step 220) toward the patient 130. For example, if the signal 114 is implemented according to the IEEE 802.11(a) protocol, the signal is generally a 2.4 GHz signal that operates at no more than 40 mW. That diagnostic signal is generated by an 802.11 compliant transmitter and needs no special modification before being transmitted as the diagnostic signal 114. Thus, in an embodiment of the invention, the device 110 is implementing the same 802.11 signal used for wireless communications, e.g., signal 112, for the diagnostic signal 114.

Utilizing signals that meet such ubiquitous protocols not only ensures that embodiments of the invention can be implemented by numerous devices, such as cell phones and laptop computers, but also permits reduced power consumption, since such protocols often implement advanced power saving techniques. For instance, where the signal is compliant with an 802.11 protocol, the signal 114 is subject to power saving mechanisms ("PSMs"), the identification and implementation of which are readily apparent to one of ordinary skill in the art. In at least one embodiment of the invention, the signal 114 is a "bursty signal," which reduces the power consumption of the device 110 while also minimizing the amount of electromagnetic radiation in the environment.

In an embodiment of the invention, the source signal 114 is a modulated signal such as a QAM with OFDM signal, the implementation of which are both well known to one of ordinary skill in the art. These modulation methods have advantages over using simpler modulation techniques such as quadrature phase-shift keying (QPSK), binary phase-shift keying (BPSK), and frequency-shift keying (FSK), which are nonetheless feasible for implementation in the present invention. The more complex the modulation of the source signal, the better background signal is created for later processing. OFDM has the advantage of having multiple carriers so that there are more strong multipath signals received. For example, the use of OFDM allows embodiments of the invention to be used in non-line of sight environments. For example, in a disaster area such as an earthquake, a patient may be buried under rubble and debris. Furthermore, it is relatively easier to derive intelligence from a noisy radio environment using such advanced modulation techniques. This occurs because non-randomness elements from many multi-paths in a background of random noise are more easily processed than non-random events over a very narrow band.

The signal 114 is then returned (step 230) from the patient as a modified signal 134. Different parts of the patient reflect components of the signal 114 back in different ways. For example, different bodily tissues, such as skin, lungs, heart, bones, etc. reflect components of the signal back differently. This is because the tissues have unique features due to varying material constituents and Doppler effects caused by different movements from the different tissues. For instance, a patient's lungs move differently than the patient's heart, and therefore the components of the signal reflected by the heart and lungs have different unique features.

After the device 110 receives the components of the signal 134 back from the patient, the received signal is then fed to a mixer, the implementation of which is apparent to one of ordinary skill in the art. The mixer is also fed (step 240) the original transmitted signal 114 as the other input, which is used to determine frequency differences between the original transmitted signal and the signal received by the device 110. The output of the mixer is a superposition of signals representing frequency differences between transmitted and received signals along with other high frequency components. The output of the mixer is then filtered (step 250) using advance mathematical techniques, which are discussed in more detail below. These filtering techniques require less processing than conventional filtering techniques, and are used to extract pertinent information from the output, depending on the specific physiological application.

In at least one embodiment of the invention, the output of the filter(s) is fed (step 260) to a digital signal processing (DSP) module, which extracts useful physiological information from the output for analysis. For example, the DSP module extracts frequency components corresponding to heartbeat and respiratory rates and displays those frequency components on a display for review. The physiological information gathered by the device 110 may be transmitted to a central monitoring unit (CMU) over the Internet or other type of communications medium, the identification and implementation of which is apparent to one of ordinary skill in the art.

Figure 3:
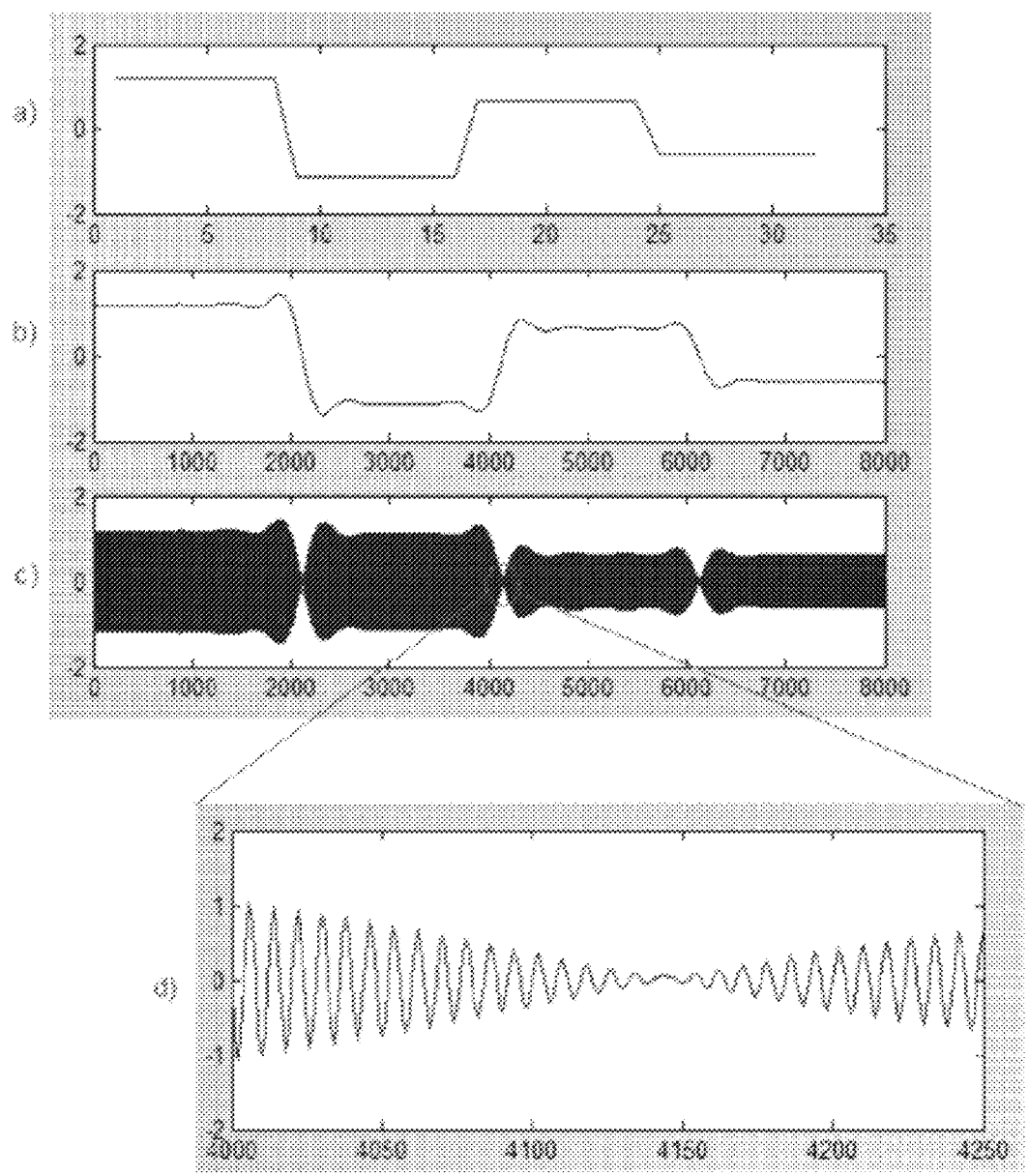
FIG. 3 illustrates the in-phase component of a base band signal, a pulse-shaped signal before it modulates the carrier, and a modulated carrier obtained by multiplying the pulse-shaped base-band signal with carrier signal.

Referring to FIG. 3, consider the in-phase component of a base band signal as shown in FIG. 3(a). The signal is pulse-shaped as shown in FIG. 3(b) before being used to modulate the carrier. Assuming a base band frequency of 10 MHz and a carrier frequency of 2.3 gigahertz, the modulated carrier obtained by multiplying the pulse-shaped base-band signal with the carrier signal is shown in FIG. 3(c) with a portion zoomed in as shown in FIG. 3(d). As seen in FIG. 3(d), the amplitude of the modulated carrier fluctuates with the base-band signal. Also, the frequency of the modulated carrier is no longer equal to the carrier frequency. Rather the frequency is spread over upper and lower side bands.

The modulated carrier can be used as a diagnostic signal 114 for Doppler based organ, e.g., heart and lung, monitoring. If the two input signals to the RF mixer are $$v_1(t) = A_1 \cdot \sin(2\pi f_1 t + \phi_1) \text{ and}$$

$$v_2(t) = A_2 \cdot \sin(2\pi f_2 t + \phi_2),$$

the output of the mixer, disregarding constant phase, is $$v_1(t) \cdot v_2(t) = \frac{A_1 A_2}{2}[\cos(2\pi(f_1 - f_2)t) - \cos(2\pi(f_1 + f_2)t]$$

After filtering out the high frequency part, the mixer output is, $$v_{out} = \frac{A_1 A_2}{2}\cos(2\pi(f_1 - f_2)t)$$

That is, $$v_{out} = \frac{A_1 A_2}{2}\cos(\omega_1 t - \omega_2 t)$$

Thus, there will be fluctuations in the mixer output if there are fluctuations in the amplitudes of the input signals or in the phase difference. In the case of an OFDM modulated carrier, both types of fluctuations are present. However, if viewed in the scale of heart beat frequency, these high-frequency amplitude and phase fluctuations can be considered as pseudo-random noise and can be eliminated by a suitably designed filter, such as a Kalman filter, as described below. Slowly varying frequency shifts (and thus phase shifts) due to the Doppler effect of heart and lung movements remain persistent and appear in the Kalman filtered output.

In an embodiment of the invention, the device 110 filters the output of the mixer using one Kalman filter and five correlation filters. A brief description about each of these filters is given below. General implementation of a correlation filter is apparent to one of ordinary skill in the art.

1. Kalman Filter

Figure 4:
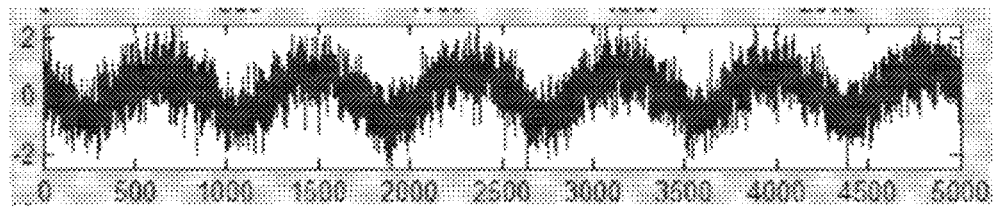
FIG. 4 illustrates the mixer output signal corrupted with strong white noise.
Figure 5:
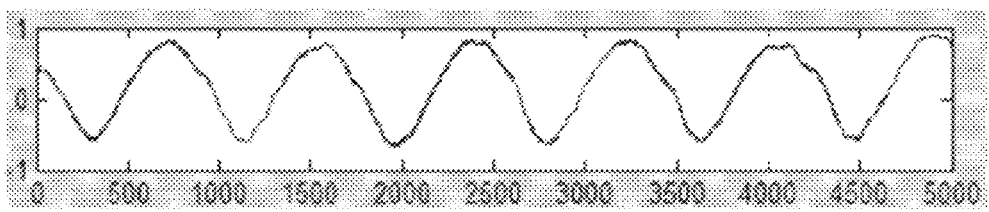
FIG. 5 illustrates the output of Kalman filter applied on the corrupted signal in FIG. 4.

The Kalman filter is used to eliminate random noise from the mixer output. A sample mixer output with strong white noise and the Kalman filtered recovered signal are shown in FIGS. 4 and 5, respectively.

2. Correlation Filters

Correlation filters are applied on rectified mixer output to detect events in the heart cycle. In an exemplary embodiment of the invention, five correlation filters are used and are described in what follows.

2.1 Heart Period Detection

Figure 6:
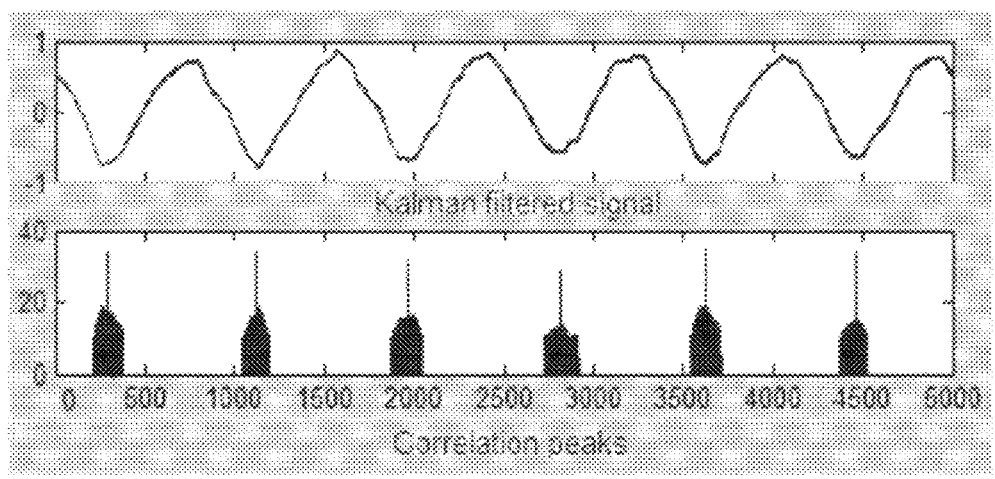
FIG. 6 illustrates the detection of heart period in a Kalman filtered signal.

A correlation filter with appropriately chosen filter coefficients is applied on the Kalman filtered signal as shown in FIG. 5. This filter produces peak values when it is convolved with lowest points of the signal. These lowest points correspond to ventricular contraction of heart. Thus any two successive peak values of the correlation filter marks a period—from one ventricular contraction to subsequent ventricular contraction. Correlation based heart period marking is shown in FIG. 6.

2.2 Events Detection

Figure 7:
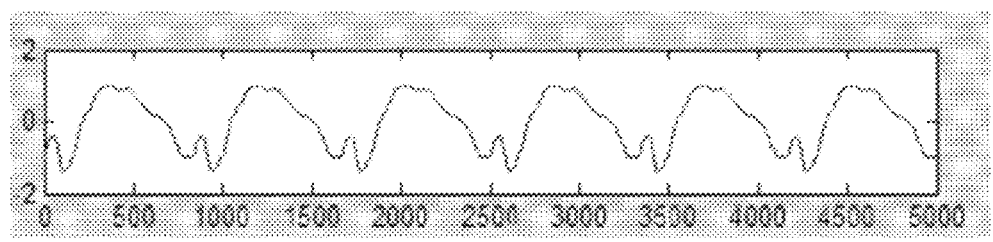
FIG. 7 illustrates computed frequency shifts corresponding to the Doppler effect.

A set of four filters detects important events within the heart period—namely atrial and ventricular contraction and relaxation. Contraction is characterized by negative frequency shift and relaxation by positive frequency shift. As the mixer output provides cosine/sine of relative phase, pure phase information is extracted from the output and differentiated to find frequency shifts. These frequency shifts correspond to frequency shifts due to the Doppler effect. FIG. 7 shows computed frequency shifts. The four correlation filters are described below.

2.2.1 Convex Curve Detection

Figure 8:
FIG. 8 illustrates detection of curvature with convex shape peaks.
Figure 8:
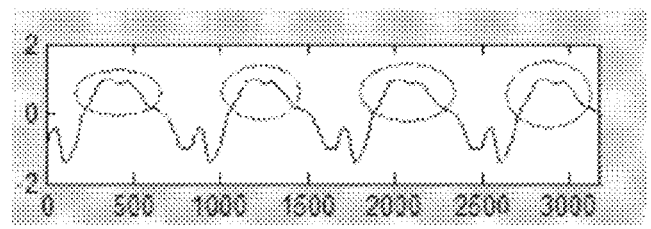

A correlation filter is designed for detection of curvature with convex shape as shown in FIG. 8. Peak values in the filter output correspond to the atrial and ventricular relaxation of heart. (Note that atrial relaxation and ventricular relaxation happen at overlapping times). FIG. 8(a) shows the correlation template. FIG. 8(b) shows candidate curves in the frequency shift signal.

2.2.2 Convex Sharp Curve Detection

Figure 9:
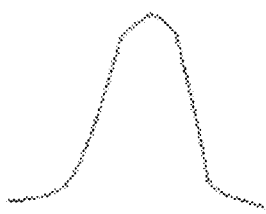
FIG. 9 illustrates detection sharp convex curves.
Figure 9:
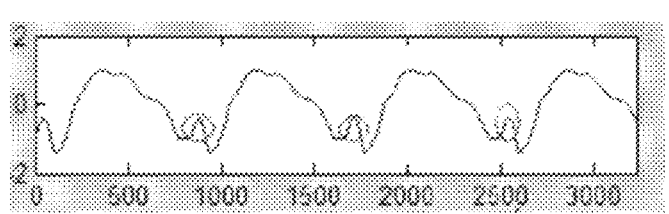

A correlation filter is designed to detect sharp convex curves as shown in FIG. 9. Peak values of this filter correspond to gap between atrial and ventricular contraction peaks. FIG. 9(a) shows the correlation template. FIG. 9(b) shows candidate sharp curves in the frequency shift signal.

2.2.3 Concave Curve Detection

Figure 10:
FIG. 10 illustrates detection of concave curves.
Figure 10:

This correlation filter detects concave curves as shown in FIG. 10. Peak values correspond to peak atrial contractions. FIG. 10(a) shows the correlation template. FIG. 10(b) shows candidate concave curves in the frequency shift signal.

2.2.4 Concave Sharp Curve Detection

Figure 11:
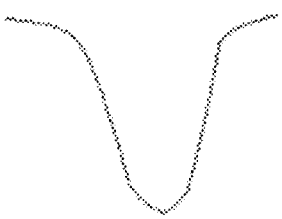
FIG. 11 illustrates detection of sharp concave curves.
Figure 11:
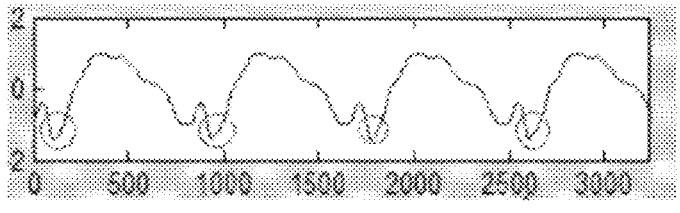

The last correlation filter detects sharp concave curves as shown in FIG. 11. Peak values correspond to peak ventricular contractions. FIG. 11(a) shows the correlation template. FIG. 11(b) shows candidate sharp concave curves in the frequency shift signal.

The techniques, systems, and methods described herein to measure heart rhythm and respiration, including, for example, the use of the Doppler effect to create a radar and post process it with filters and then apply various state machines, can be extended to many other applications. For example, in some embodiments, other Arrhythmias, such as Fibrillation, Super Ventricular Tachycardia, Ventricular Tachycardia, and Strength of the pulse, are detected to help determine the efficiency of the heart. The breathing rate and heart rate of a patient can also be determined. In other embodiments, the techniques, systems, and methods are used in applications unrelated to medicine, such as determining when someone enters a room. As discussed above, the sensor device does not have to be in direct physical contact with a patient. Therefore, in some embodiments, the sensor device can be used to determine nervousness, or excitement in a variety of situations from security evaluations to reaction to stimulus, such as in movies.

Experimental Results

Figure 12:
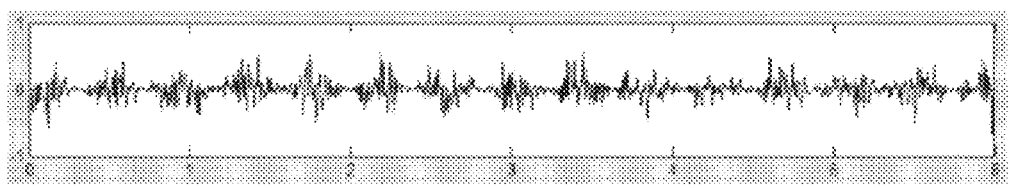
FIG. 12 illustrates envelopes in the down-converted signal (in phase) due to Doppler effect.
Figure 13:
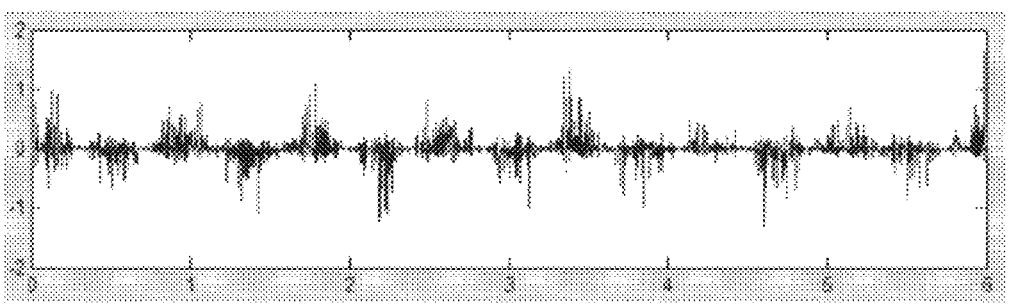
FIG. 13 illustrates the product of the original baseband and the down-converted signal.

Doppler shift has a significant effect on the carrier frequency due to the relatively small wavelength of the carrier, while its effects on baseband signal components are negligible due to comparatively longer wavelengths. Because of the phase changes of the carrier due to Doppler effect, periodic rotations are noticed in the constellation diagram of the down-converted signal. This is common physics shared by both OFDM and non-OFDM based transmissions. By processing these periodic rotations, the movement frequencies of the sources of the Doppler effect can be estimated. In the present case, sources of the Doppler effect are moving organs such as the lung and heart. The I and Q parts of the down-converted signal exhibit envelops due to rotations as shown in FIG. 12. If one takes a Fast Fourier Transfer (FFT) or similar frequency component measurement of this down-converted signal, no useful information can be achieved, because the signal is pseudo noisy. In order to extract useful information from the envelopes, multiply this with the original baseband signal. The result is similar to the signal shown in FIG. 13, which is periodic with alternating positive and negative envelops. Clear peaks at Doppler shifts can be seen in the corresponding frequency spectrum. The intermittent nature of WiFi transmission due to TDD does not affect the frequency spectrum except slightly weakening the peaks at Doppler shifts and introduction of a new peak at the TDD frequency.

Figure 14:
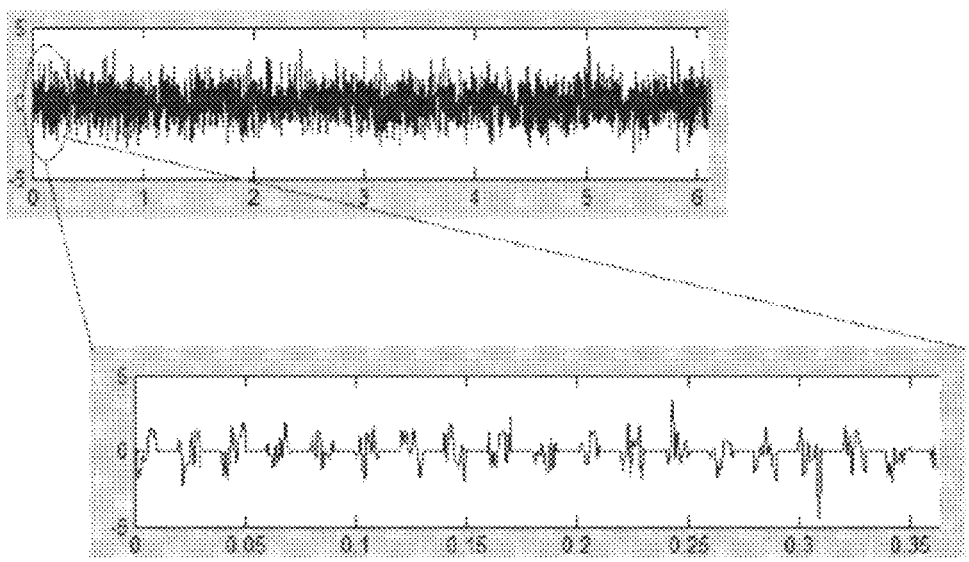
FIG. 14 illustrates a baseband transmission signal.
Figure 15:
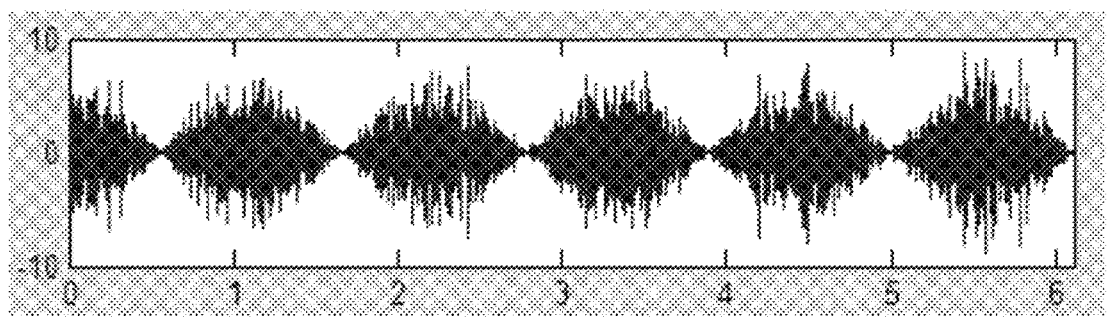
FIG. 15 illustrates envelopes in the RF signal due to the Doppler effect.
Figure 16:
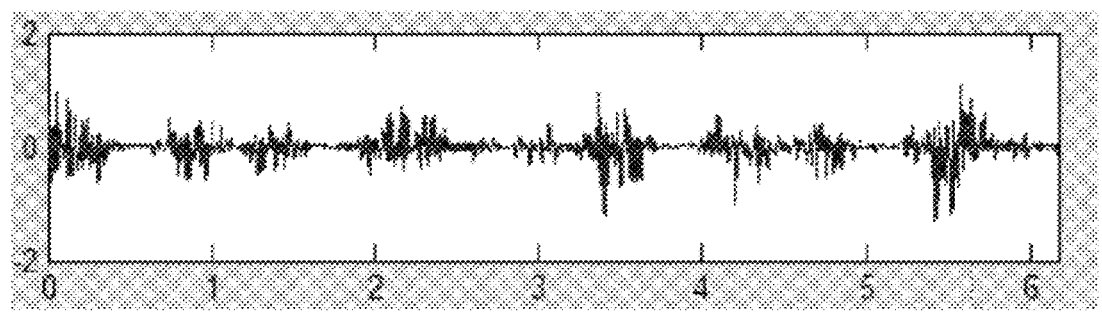
FIG. 16 illustrates the down converted signal.
Figure 17:
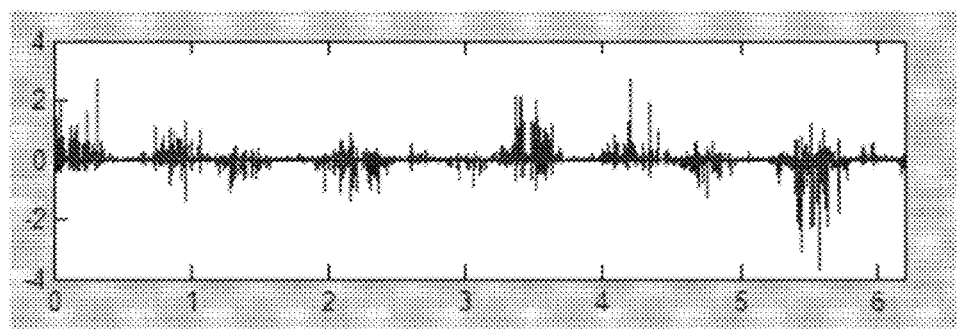
FIG. 17 illustrates the product of the baseband return signal and the original baseband transmission signal.
Figure 18:
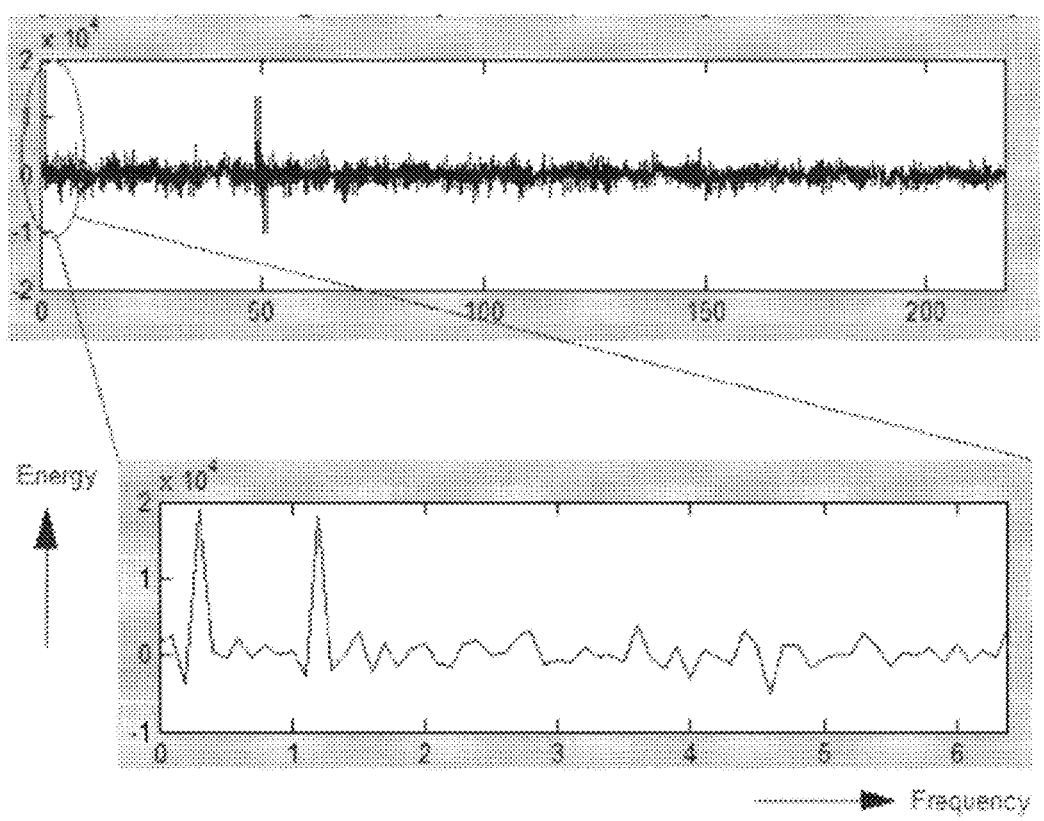
FIG. 18 illustrates the FFT of the product of baseband transmission and the return signals.

The WiFi RF transmission for Doppler effect based heartbeat and lung rate detection was simulated as follows. The baseband TX signal is shown in FIG. 14. The modulated carrier signal with very low frequency envelopes due to Doppler effects of heart and lung movements is shown in FIG. 15. Upon down-conversion of the RF signal, envelops are seen in the in the baseband RX signal as shown in FIG. 16. The down-converted signal is multiplied with the original signal to obtain the result shown in FIG. 17. Finally FFT is performed on the product signal shown in FIG. 17. The resulting frequency spectrum is shown in FIG. 18. Although for mathematical analysis, FFT has been used to estimate energy at different frequencies, a Goertzel algorithm was used in the actual experiment.

As is apparent, embodiments of the invention have several advantages over current sensing technologies. Embodiments of the invention are implemented using wireless technology, and therefore do not require electrodes and physical human contact to function. Because embodiments of the invention operate using standard wireless communication protocols, inexpensive and readily available devices such as cell phones and WiFi complaint devices can be used to implement embodiments of the invention. Also, because the filtering techniques are computationally efficient, real-time and/or near real-time scanning and/or detection can take place.

The present invention can be used as a non-line of sight motion detector. As an example, it can be used for an intrusion alarm in a house or office—the range of detection being dependent on the range of the modulated carrier, e.g., WiFi signal. If implementing a microwave signal, it can go through walls and can cover a much larger area than ultrasonic or infra-red detection. Regardless of the type of source signal, the movement of organs of a person within a respective detection range can be detected by the present invention, thereby signaling the presence of that person.

In a military application, the present invention can be used to detect the movement of aircraft such as through a pass in the mountains where there is no direct line of sight to the radar. It can be used to detect stealth aircraft that diffuse radar signals or absorb them since the equilibrium of the infinite multi-paths will be disturbed by the aircraft moving.

In the medical area of heart and respiration monitoring, the present invention is directly measuring the motion characteristics of the hearts instead of inferring the motion of the heart from the electrical signals shown on an EKG. The motion characteristics of the heart as a result of the electrical signals in the heart have been well documented; a reverse function can detect variance in the expected movement in time, speed, and distance. A pseudo EKG can be generated so that it can be compared to normal characteristics of an EKG such as whether the heart is actually moving when expected as well as providing the traditional measurements of the various characteristics of an EKG. In this way it has some of the characteristics of an EKG and an Echo Cardiogram.

Figure 19:
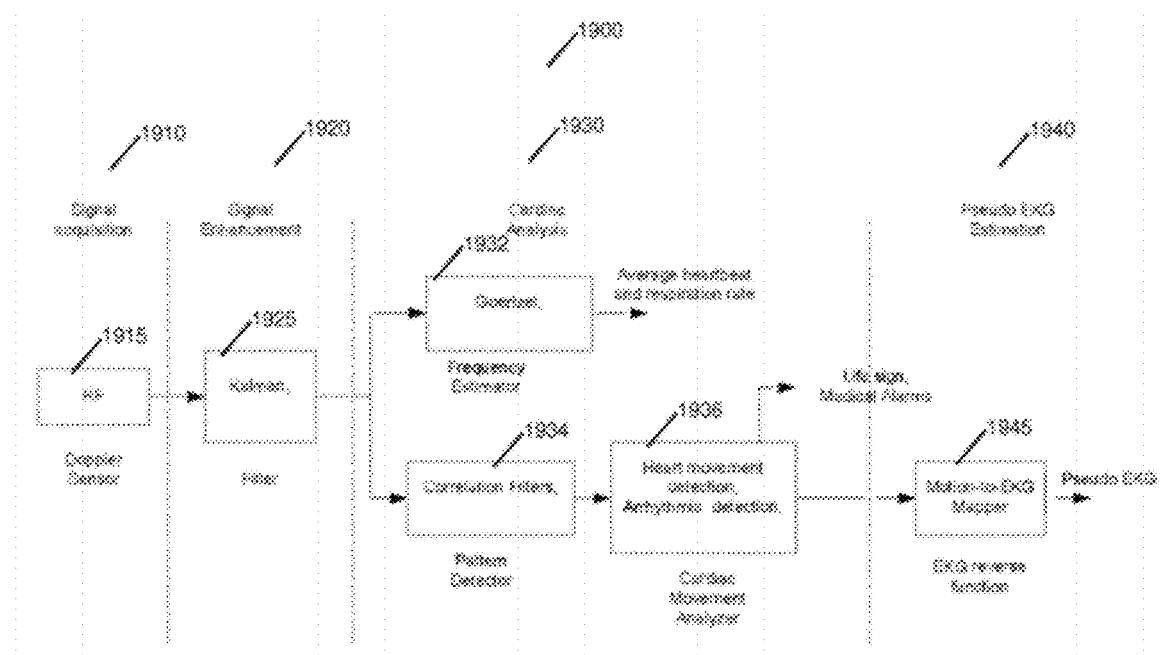
FIG. 19 illustrates a high-level diagram of a Doppler radar-based physiology monitoring device according to embodiment of the invention.

FIG. 19 illustrates a high-level diagram of a Doppler radar-based physiology monitoring device 1900 according to embodiment of the invention. The physiology monitoring device 1900 comprises RF signal acquisition circuitry 1910, signal enhancement circuitry 1920, cardiac and pulmonary analysis circuitry 1930, and pseudo-EKG estimation circuitry 1940. The signal acquisition circuitry 1910 comprises an RF Doppler-sensor 1915 for detecting the diagnostic signal 114 and the modified signal 134 discussed above. These signals are enhanced using the signal enhancement circuitry 1920, which comprises a Kalman filter 1925. The enhanced signal is fed into a frequency estimator 1932, such as an estimator based on the Goertzel algorithm, the implementation of which is apparent to one of ordinary skill in the art, which is a digital signal processing technique for identifying frequency components of a signal. The frequency estimator 1932 is used to determine the average heartbeat and/or respiration rate of a suitably located patient. The enhanced signal is also fed into a pattern detector 1934, which may include one or more correlation filters 1934, to detect patterns associated with the movement of organs in the patient such as, but not limited to a heart arrhythmia. Detection circuitry 1936 is implemented to correlate the detected patterns with certain conditions such as an arrhythmia. The frequency estimator 1932, pattern detector 1934, and detection circuitry 1936 are included within the cardiac and pulmonary analysis circuitry 1930. The detection circuitry 1936 may be coupled to one or more life signs or medical alarms (not shown). The pseudo-EKG estimation circuitry 1940 comprises a motion-to-EKG mapper 1945 to generate a pseudo EKG.

Figure 20:
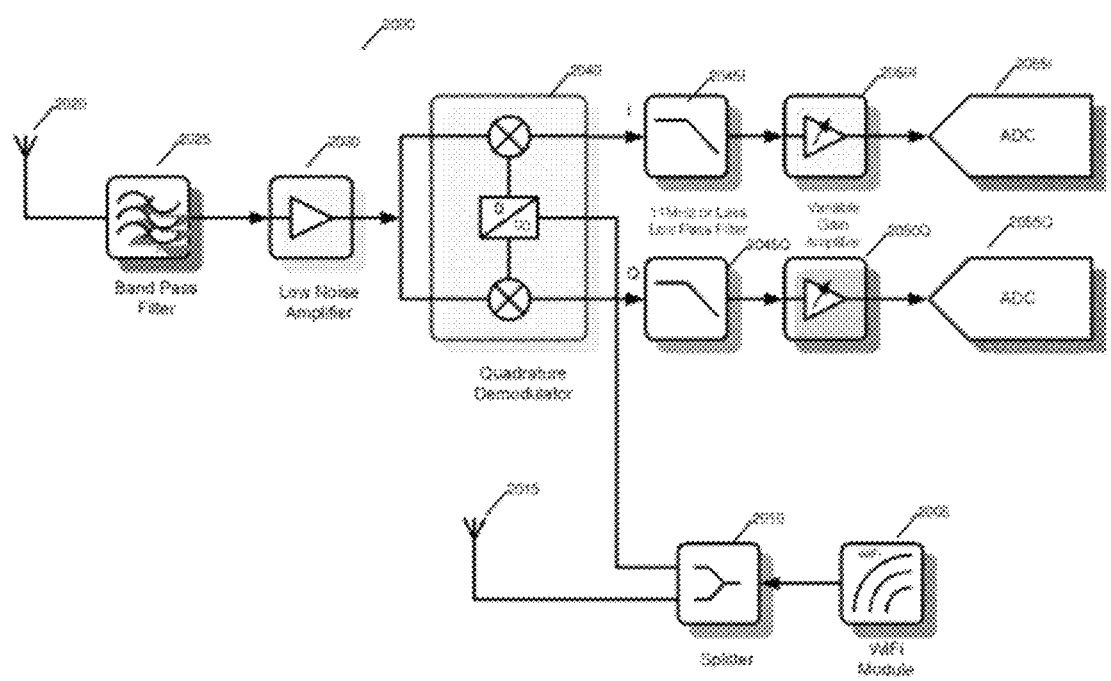
FIG. 20 illustrates an RF diagram of a Doppler radar-based physiology monitoring device according to embodiment of the invention.

FIG. 20 illustrates an RF diagram of a Doppler radar-based physiology monitoring device 2000 according to embodiment of the invention. The physiology monitoring device 2000 comprises a WiFi module 2005 to generate the diagnostic signal 114. The diagnostic signal 114 is split by a splitter 2010 with one signal part being transmitted into the surrounding area through a suitable antenna 2015. A receiving antenna 2020 is provided to detect the modified signal 134. The detected modified signal 134 is processed through a band-pass filter 2025, which attenuates unwanted frequencies, and a low noise amplifier 2030, which amplifies the modified signal 134 after it leaves the band-pass filter 2025. The modified signal 134 and the other part of the diagnostic signal 114 are fed into a quadrature demodulator 2040, the implementation of which is apparent to one of ordinary skill in the art. The quadrature demodulator 2040 recovers the I and Q channels, which are each processed by a low-pass filter 2045I or 2045Q, a variable gain amplifier 2050I or 2050Q, and an analog-to-digital converter 2055I or 2055Q, respectively. The digital output of the converters 2055I and 2055Q undergo further processing as noted above to determine heart and respiratory rates, detect arrhythmias, etc. of the patient 130.

Figure 21:
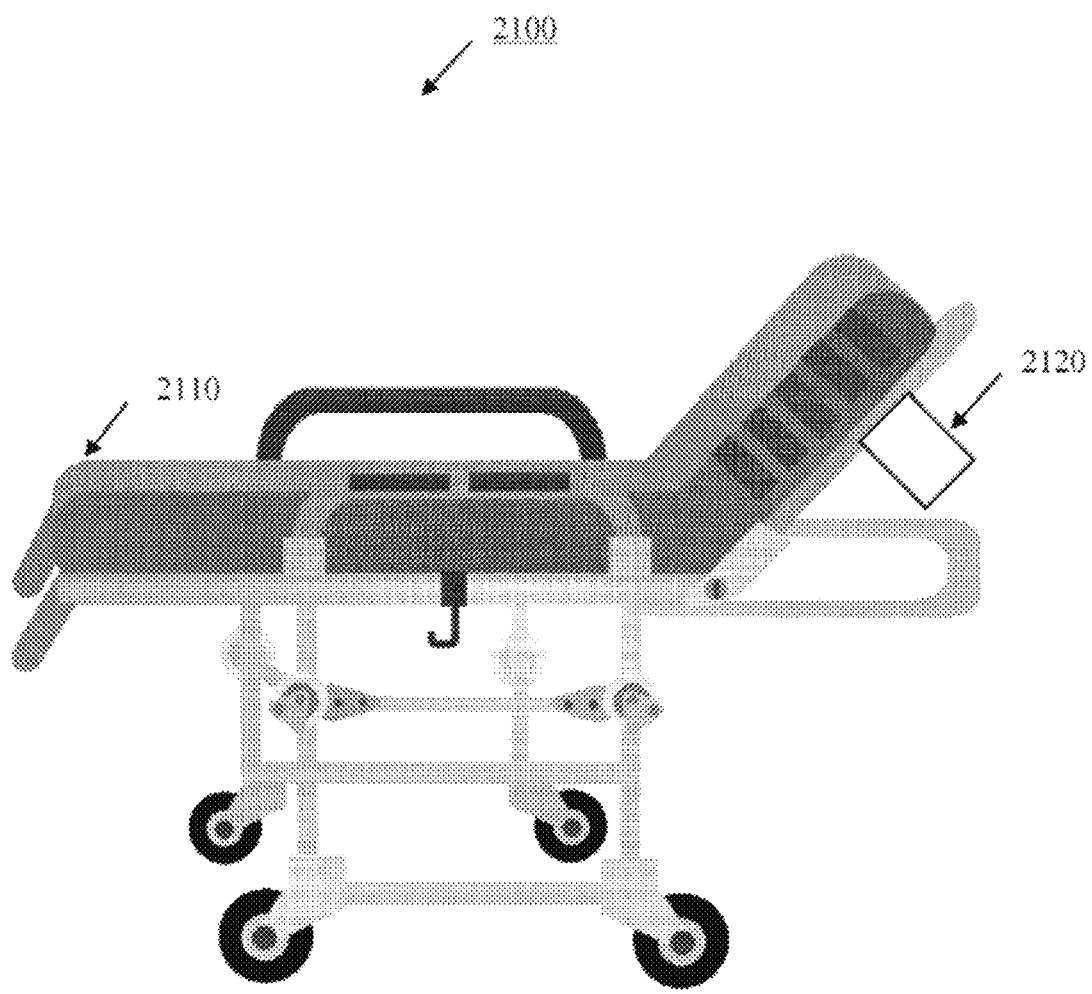
FIG. 21 illustrates a physiology monitoring system according to an embodiment of the invention.

FIG. 21 illustrates a physiology monitoring system 2100 according to an embodiment of the invention. The physiology monitoring system 2100 comprises a hospital bed 2110 and a physiology monitor 2120. The inclusion of the hospital bed 2110 is exemplary only and can replaced with any type of medical equipment where a patient can be located such as, but not limited to a gurney, a stretcher, a trolley, an examination table, a back board (sometimes referred to as a spine board), a cot or portable bed, an infant bed or crib, an incubator, and various forms of furniture and other medical devices. The physiology monitor 2120 is coupled to the bed 2110. For example, in an embodiment of the invention, the physiology monitor 2120 is disposed on the bottom of the bed 2110 as shown. Here, the physiology monitor 2120 is located on the underneath side of the bed 2110 opposite of where a patient's scapular, i.e., shoulder blade, would be located if the patient was lying back-down on the bed 2110. This location is preferable as it permits the physiology monitor 2120 to be placed close to the patient's heart and lungs. In an embodiment of the invention, the physiology monitor 2120 comprises a directional antenna (not shown) to efficiently direct the diagnostic signal 114 to the patient and width of the bed while limiting the range of the diagnostic signal 114, e.g., within two or three feet, to prevent interference by the presence of other persons in the vicinity of the bed 2110.

In at least one embodiment of the invention, the device 110 comprises a means for motion detection (not shown) such as, but not limited to a 3-axis accelerometer or the like, the identification and implementation of which is apparent to one of ordinary skill in the art. As used herein, "motion detection" generally refers to the ability to sense whether a human has moved and if so, the direction and magnitude of such movement at any given instant in time. This includes "fall detection," which refers to a patient such as an elderly user of the device 110 having fallen or moved suddenly and perhaps harmfully due to, for example, an accident or syncope, which is a partial or complete loss of consciousness and posture. Falls, syncope, and the associated complications are among the most serious problems that face the elderly population. The most common underlying causes and risk factors for falls include muscle weakness, gait and balance problems, visual impairment, cognitive impairment, depression, functional decline, and particular medications (especially in the presence of environmental hazards). Studies have identified the relative risks for these factors that enable a fairly accurate prediction of who is at high risk for falls and what areas to target for falls-prevention activity. Certain studies have shown that 64 percent of patients with recurrent syncope sustained an arrhythmia at the time of their sudden loss of consciousness.

In operation, once a fall or other irregular movement is detected by the accelerometer, the device 110 begins monitoring and preferably recording (either locally or remotely by a CMU) various functions of the patient's heart and lungs as detailed above. In other words, a fall may trigger the operation of the device 110 according to an embodiment of the invention. The physiological data gathered by the device 110 can be transmitted in real-time to CMU to convey the data as well as the occurrence of the fall itself to a medical provider or health care professional. In another embodiment of the invention, the device 110 includes a button that a user can press to activate monitoring of physiological functions.

In another embodiment of the invention, the device 110 (including accelerometer) is implemented in connection with another medical data acquisition device such as, but not limited to a weight scale or a blood pressure monitor to collect and transmit a range of medical data associated with the patient using the device 110 and transmit such to a remote server, e.g., CMU. In the case of a weight scale, the weight scale comprises a vibration source for emitting a vibration at a predetermined frequency. When a patient wearing the device 110 steps onto the weight scale, the vibration is transmitted from the weight scale, through the patient, and to the device 110, which the accelerometer detects. The device 110 then measures the particular frequency of vibration and transmits this information to the CMU, which is also in communication with the scale as well. Based on the measured frequency, the CMU is able to know that the same patient wearing the device 110 is also the same patient being weighed and is thus able to store both weight and the physiology data measured by the device 110 into a record corresponding to the particular patient. One of ordinary skill in the art recognizes that the use of a scale or blood pressure monitor is exemplary only and that other medical data acquisition devices may be implemented with vibration sources to achieve the same objective of recording various medical information.

The following example is provided to better illustrate the above acquisition technique. The weight scale receives a magnitude of a vibration frequency from the CMU of 57 Hz. The patient wearing the device 110 steps on the scale, which vibrates at 57 Hz at some point. The device 110 detects the vibration of 57 Hz and transmits this to the CMU. The CMU then knows that the particular scale, which vibrated at 57 Hz, is weighing the same patient weighing the device 110, which detected the 57 Hz. Both weight data and physiology data acquired by the device 110 are associated with one another and the corresponding patient—this information can then be stored into a respective electronic medical record associated with the patient. If the device 110 further includes a biometric sensor, the CMU is able to acquire the respective biometric information sensed and determine the identity of the patient if the appropriate corresponding biometric record of that patient already exists.

At some point afterward, the scale switches to a different vibration frequency such as 61 Hz. A second patient (using the same device 110 as the first patient was using or a different device 110) then steps on the scale and is vibrated at 61 Hz, which is detected by the accelerometer of the worn device 110. The CMU is then able to determine that the second patient's weight from the scale should be associated with the information acquired from the device 110 being worn by the patient at that time. One of ordinary skill in the art recognizes that numerous permutations exist on the above technique for acquiring medical data from other medical devices used in connection with the device 110. For example, as described above, the medical device, e.g., scale, blood pressure monitor, oximeter, breath analyzer, etc., may request the CMU to identify a particular vibration frequency. In another example, the medical device may select a vibration frequency and transmit the magnitude of the known frequency to the CMU rather than requesting it. The medical device may change vibration frequencies at predetermined intervals—after every 30 or 60 seconds the medical device switches to a new frequency.

In a military scenario, the device 110 may be included as part of a larger physiologic monitoring system for monitoring the health and situation of a soldier in the field. For example, a number of accelerometers are positioned in the uniform, garment, or shielding worn by a soldier along with the device 110 to monitor movement and vital signs. The accelerometers are positioned at key points, the identification of which is apparent to one of ordinary skill in the art, of the soldier's body such as feet, knees, waist, hands, elbows, shoulders, and head, or any combination thereof. The accelerometers along with the device 110 are in communication with a CMU. The CMU is thus able to determine the soldier's motion (e.g., running, walking, stationary, direction, and location), mortality, limb loss, consciousness, tremors due to shock and extreme environmental conditions, fatigue (as a function of posture, gate, and other vital signs), physical and concussive impact, weapons discharge, injury via gate analysis, and full body motion including arms and legs with stride analysis and/or visualization. The accelerometers may be sewn/integrated into the soldier's clothing, belts, helmets, or boots, and can be connected via a wired bus in the clothing or can communicate wirelessly to a gateway located in the belt. The gateway may store the acquired data for later inspection (such as a "black box") or may transmit the acquired data to the CMU in real-time or near real-time. The device 110 may be worn as a pendant around the neck of the soldier—thereby, replacing the function of a soldier's conventional "dog-tag."

Military applications have special considerations. For example, any physiological monitoring system including the device 110 must not be detectable by the enemy. Accordingly, any radio diagnostic frequency emitted by the device 110 must have a relatively low power, e.g., can only be detected within a small radius, e.g., a 2-3 foot sphere, around the solider. In some scenarios, the diagnostic signal of the device 110 should not be a widely-known protocol such as IEEE 802.11(x) in places where such a signal would not normally exist, e.g., in desert conditions. In other scenarios, this may be less of a concern in areas where the same protocols are normally implemented, e.g., in urban environments. In an alternative embodiment, the diagnostic radiation appears as random background noise to an observer. Moreover, any communication from the device 110 to a CMU should use secure military communications, the identification and implementation of which is apparent to one of ordinary skill in the art, to prevent detection of the soldier or unauthorized access to the data being communicated. As noted above, the present invention is able to harness the secure military communication signal (implemented between the device 110 and the CMU) as the diagnostic signal.

The physiology monitoring techniques disclosed herein may also be used as a means to identify particular individuals as every person's heart has a unique data signature that is detectable. In other words, the device 110 is capable of capturing the unique elements of heart movement to create a unique identification. For example, the frequency and period of ventricular contractions (as well as particular arrhythmias) are unique to each individual. Such an identification technique can be combined with the vibration sensor for positive identification for access control purposes—e.g., the user of the device 110 may place their hand on a wall plate that vibrates at a particular frequency to gain access to a secure area.

In another embodiment, improving the overall system 100 for detecting a signal from a diagnostic RF source reflected from slow moving objects may be achieved by enhancing the bandwidth of the signal prior to the DSP module step (step 260) of FIG. 2. Furthermore, novel statistical integration techniques may be applied to the reflected signal to improve the effectiveness of differentiating the Doppler effect on the reflected signal from other signals.

In one medical related implementation, as shown in the system 100 of FIG. 1, a transmitted diagnostic signal $S_T$ 114 generated from a device 110 is incident upon a first part of a patient 130 such as, for example, the patient's chest and a different portion of the signal $S_T$ is reflected from other bodily tissues in motion of the patient, including but not limited to the chest, lung and heart surfaces. The reflected signal 134 is received at an RX antenna of the device 110.

Figure 22:
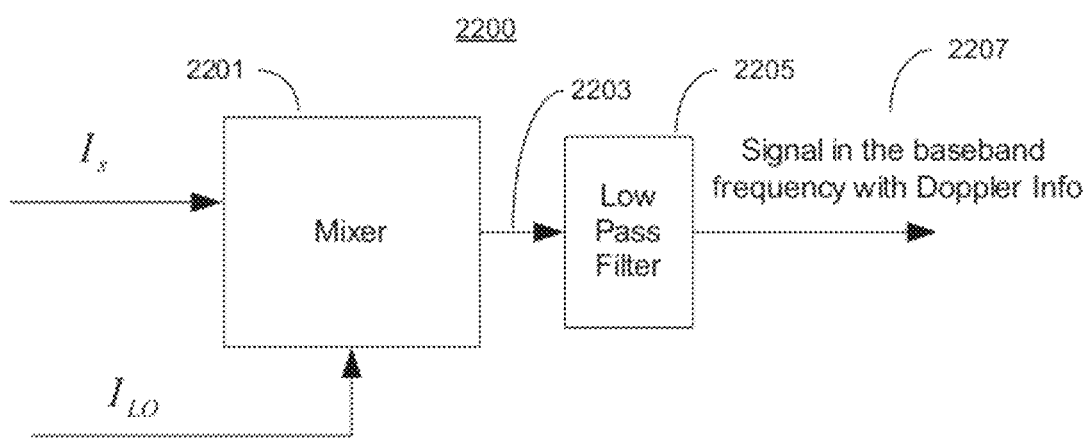
FIG. 22 illustrates an extraction of Doppler information from RF signal using a mixer.
Figure 23:
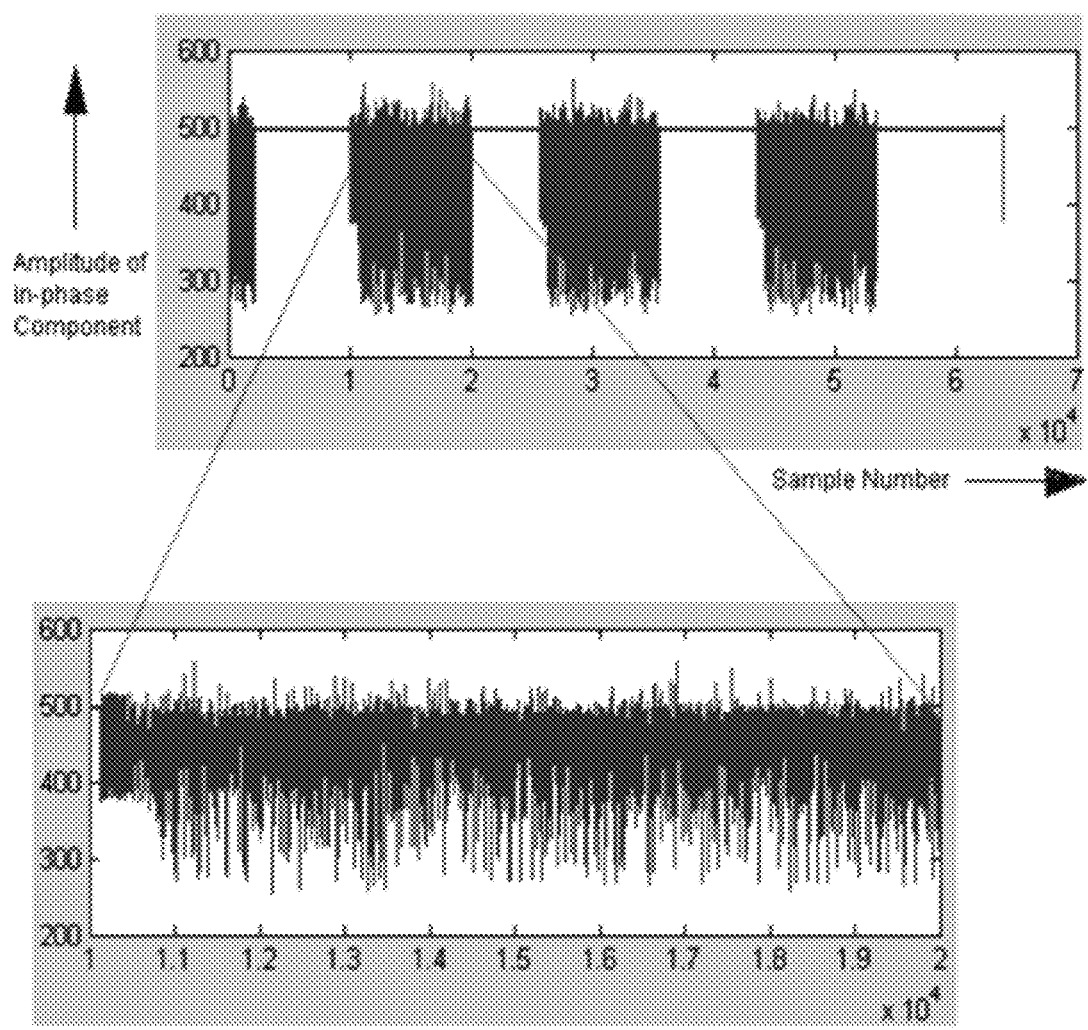
FIG. 23 illustrates a mixer output (in-phase component)
Figure 24:
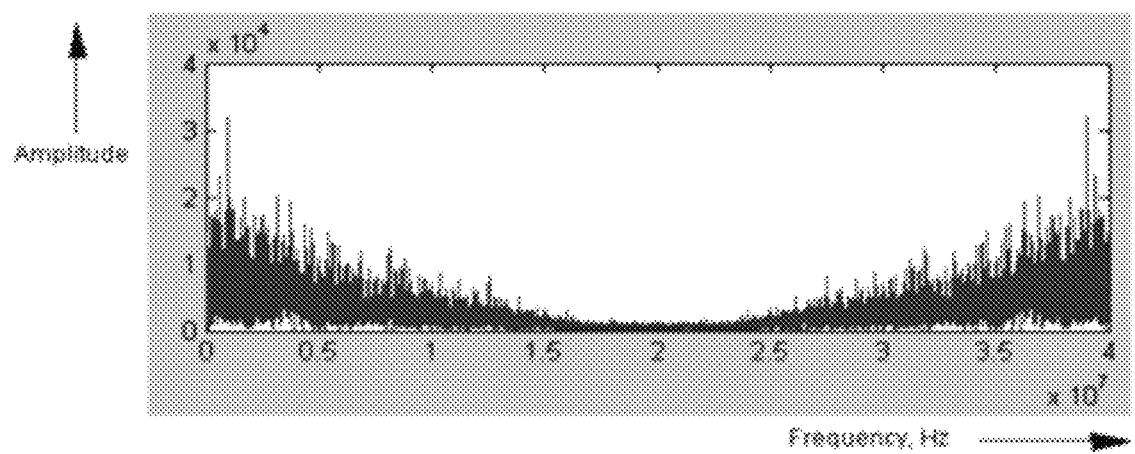
FIG. 24 illustrates an FFT analysis of the mixer output.

In general, reflected signals may undergo a Doppler effect as characterized by a decrease or increase in a received frequency from an electromagnetic radiation source, as compared to a frequency emitted from the original source signal. Although the Doppler effect from fast moving objects are detectable by conventional means such as optical and radar systems, in a slow moving object, such as in the heart or lung, generate low bandwidth signals, making detection of the Doppler effect of the slow moving object a challenge due to low bandwidth spread. FIGS. 22-24 describe a system and method for increasing the detection of the Doppler effect of a slow moving object.

FIG. 22 illustrates one implementation of a system 2200 for improving the Doppler shift associated with a slow moving object. The system 2200 comprises a mixer 2201 and a low pass filter LPF 2205, where one input $I_{LO}$ to the mixer 2201 may be any band-limited RF signal and the other input $I_s$ to the mixer 2200 may be the same RF signal but shifted due to the Doppler Effect. The mixer output 2203 is a superposition of low frequency signals near baseband frequency and high frequency signals centered near $2f_c$, where $f_c$ is a carrier frequency generated by a device 110 as shown in FIG. 1. The high frequency components may be suppressed by a low pass filter to extract a portion of the signal information 2207. Using statistical sampling methods, the signal information may be refined, evaluated and correlated to the physiological response of the patient's organs in real-time.

The above diagnostic signal in system 2200 may be implemented with a variety of wireless protocols, including WiFi, WiMAX, and OFDM. These protocols have beneficial features for detecting slow moving objects, including sensitivity to the Doppler shift of the received signal and substantially even levels of energy distributed across the entire band. When the object in consideration moves toward the receiver, the frequency of the signal components throughout the bandwidth increases due to Doppler shift. As such, the full bandwidth of signal moves toward higher frequency. At a particular frequency point, if the energy versus frequency distribution is a decreasing function, then this Doppler shift will increase energy at the frequency in consideration. However, at an earlier frequency, the energy will decrease. On the average, it is expected that energy distribution at the edge will be a decreasing function. In that case, it is expected that the energy at the band-edge will increase, when the object moves toward the receiver. When the object moves away from the receiver, the situation is reversed. Thus, the energy is expected to decrease at the band edge when the object moves away from the receiver.

One advantage of the system 2200 is that the bandwidth of the output of the low pass filter is double the original baseband bandwidth. In other words, if the bandwidth of $I_s$ as well as of $I_{LO}$ is W then the bandwidth of low pass filter is 2W. Thus, an object, such as the heart, having a rate of 2 Hz may be doubled to 4 Hz, wherein 4 Hz may be further doubled to 8 Hz, 8 Hz to 16 Hz, and so on. The bandwidth of the signal may be characterized as a signal having a center frequency $f_c$, a lower band edge frequency $f_l$, and an upper band edge $f_h$, where the bandwidth is defined by $f_h-f_l$. Useful Doppler effect information (i.e., heart rate, lung expansion, etc.) typically occurs along the band edges of a signal when estimating Doppler shift from the change in the energy distribution across OFDM bandwidth due to object movement. As mentioned earlier, when the object in consideration moves toward the receiver, the full bandwidth of signal moves toward higher frequency and vice-versa. OFDM signal is quite evenly distributed across the bandwidth. Therefore, change in the energy at frequencies within the bandwidth may not be appreciable. However, it is expected that energy distribution at the edge is a decreasing function of frequency. Therefore, change in energy due to Doppler shift would be appreciable around the band-edge. As bandwidth increases, the band edge frequencies ($f_h$ and $f_l$) are moved away from the center frequency $f_c$, making the Doppler effect due to the relative motion of the heart, for example, easier to detect in the system 2200 than in other conventional systems.

The mixer 2201 doubles the bandwidth and implements equations 1-6 below. The mixer 2201 multiplies the signals appearing at the input ports $I_s$ and $I_{LO}$, which is necessary to realize the equations. Suppose the original baseband signal is $$S_b = \sum_k a_k \cos(2\pi f_k t) + b_k \sin(2\pi f_k t) \quad (1)$$

Then for a carrier signal $$S_c = a_c \cos(2\pi f_c t), \quad (2)$$

the transmitted RF signal is $$S_T = S_c \cdot S_b$$
$$= \sum_k a_c a_k \cos(2\pi f_c t)\cos(2\pi f_k t) + a_c b_k \cos(2\pi f_c t)\sin(2\pi f_k t)$$

On simplification, we obtain, $$S_T = \sum_k \left[ \begin{array}{l} A_k\{\cos(2\pi(f_c + f_k)t) + \cos(2\pi(f_c - f_k)t)\} + \\ B_k\{\sin(2\pi(f_c + f_k)t) - \sin(2\pi(f_c - f_k)t)\} \end{array} \right] \quad (3)$$

Where, $$A_k = \frac{a_c a_k}{2} \text{ and } B_k = \frac{a_c b_k}{2}.$$

For mathematical simplicity, it is assumed that the received signal originates from a single moving object. If the instantaneous Doppler shift is $f_d^{(k+)}(t)$ for the frequency ($f_c+f_k$) and $f_d^{(k-)}(t)$ for the frequency ($f_c-f_k$), then, ignoring the overall phase, the received signal may be given by, $$S_R = \sum_k \left[ \begin{array}{l} A_k\{\cos(2\pi(f_c + f_k + f_d^{(k+)})t) + \cos(2\pi(f_c - f_k + f_d^{(k-)})t)\} + \\ B_k\{\sin(2\pi(f_c + f_k + f_d^{(k+)})t) - \sin(2\pi(f_c - f_k + f_d^{(k-)})t)\} \end{array} \right] \quad (4)$$

Now, if $S_T$ and $S_R$ are fed into inputs $I_{LO}$ and $I_s$, respectively, of the mixer, the output of the mixer $O_M$ can be given by, $$O_M = S_R \times S_T = \quad (5)$$
$$\sum_k \sum_l [A_{kl}\{\cos(2\pi(2f_c + f_k + f_l + f_d^{(d+)})t) + \cos(2\pi(f_k - f_l + f_d^{(d+)})$$
$$t) + \cos(2\pi(2f_c + f_k - f_l + f_d^{(d+)})t) + \cos($$
$$2\pi(f_k + f_l + f_d^{(d+)})t) + \cos(2\pi(2f_c - f_k + f_l + f_d^{(d-)})t) +$$
$$\cos(2\pi(-f_k - f_l + f_d^{(d-)})t) + \cos(2\pi(2f_c - f_k - f_l + f_d^{(d-)})$$

-continued $$t) + \cos(2\pi(-f_k + f_l + f_d^{(d-)})t)\} +$$
$$B_{kl}\{\sin(2\pi(2f_c + f_k + f_l + f_d^{(d+)})t) -$$
$$\sin(2\pi(2f_c + f_k - f_l + f_d^{(d+)})t) + \ldots\} +$$
$$C_{kl}\{\cos(2\pi(f_k - f_l + f_d^{(d+)})t) - \cos(2\pi(f_c + f_k + f_l + f_d^{(d+)})t) -$$
$$\cos(2\pi(f_k + f_l + f_d^{(d+)})t) +$$
$$\cos(2\pi(2f_c + f_k - f_l + f_d^{(d+)})t) -$$
$$\cos(2\pi(-f_k - f_l + f_d^{(d-)})t) +$$
$$\cos(2\pi(2f_c - f_k + f_l + f_d^{(d-)}t) + \cos(2\pi(-f_k + f_l + f_d^{(d-)})$$
$$t) - \cos(2\pi(2f_c - f_k - f_l + f_d^{(d-)})t)\}]$$

Upon eliminating high frequency components via a low pass filter, for example, the resulting output mixer signal $O_M$ may be further simplified as, $$O_M = \qquad (6)$$
$$\sum_k \sum_l [A_{kl}\{\cos(2\pi(f_k - f_l + f_d^{(d+)})t) + \cos(2\pi(f_k + f_l + f_d^{(d+)})t) + \cos(2\pi(-f_k - f_l + f_d^{(d-)})t) +$$
$$\cos(2\pi(-f_k + f_l + f_d^{(d-)})t)\} + B_{kl}\{\ldots\} +$$
$$C_{kl}\{\cos(2\pi(f_k - f_l + f_d^{(d+)})t) - \cos(2\pi(f_k + f_l + f_d^{(d+)})t) -$$
$$\cos(2\pi(-f_k - f_l + f_d^{(d-)})t) + \cos(2\pi(-f_k + f_l + f_d^{(d-)})t)\}]$$

In Eq. (6), $0 \le f_k \le W$ and $0 \le f_l \le W$. Assuming that $f_d^{(k+)} \ll W$ and $f_d^{(k-)} \ll W$, the bandwidth of $O_M$ is determined by solving for $\max(|f_k+f_l|) - \min(|f_k-f_l|)$, which is $2W-0=2W$, or double the original baseband bandwidth.

A zooming function can be accomplished using multiple mixers in a cascaded system creating a Doppler microscope. Input to the cascaded system has an embedded Doppler frequency shift $f_D$ for a received signal reflected from a heart or lung. $f_D$ can be input into an $I_s$ and $I_{LO}$ of a first mixer. The output of the first mixer is doubled (2 $f_D$) and can be passed through a bandpass filter. 2 $f_D$ can be input into an $I_s$ and $I_{LO}$ of a second mixer, outputting 4 $f_p$. The process can be repeated (e.g., a third mixer would output 8 $f_p$). Frequency zooming is advantageous in handling very low frequency components of the signal, for example heartbeat and respiration rates having nominal values of 1.2 Hz and 0.3 Hz respectively. Frequency zooming can be used to convert slowly varying signal to signal with higher frequencies. For example, the frequency of the respiration signal (0.3 Hz) can be converted to 0.3*2=0.6 Hz, or 0.3*4=1.2 Hz or to higher frequencies, $0.3*2^n$, n=1, 2, 3 . . . .

FIGS. 23-24 illustrate empirical results of a frequency spectrum response supporting a 2× increase of the original baseband bandwidth, using a WiFi transmitted diagnostic and Doppler received signals. In FIG. 23, a spectral response at the mixer output, as indicated by amplitudes of the in-phase component from as a function of various measured samples, is produced by feeding a WiFi TX transmitted signal $I_{LO}$ and a Doppler RX received signal $I_s$ inputs to the mixer. This experimental result may be used as a basis for comparison to support a 2× increase in baseband bandwidth. Specifically, FIG. 22 shows a snapshot of mixer output. A portion of the signal is zoomed in FIG. 23. An FFT analysis of the signal in FIG. 23 is given in FIG. 24. As an ADC sampling frequency of 40 MHz, maximum frequency component in the ADC output is 20 MHz. Therefore, no frequency higher than 20 MHz is expected in the FFT output. This is indeed reflected in FIG. 24 (energies at frequencies from 20 MHz to 40 MHz simply being reflection of the energies at 0 MHz to 20 MHz). However, it is noticed that non-zero energy components are present throughout the band from 0 to 20 MHz. As the original bandwidths at ports $I_s$ and $I_{LO}$ are 11 MHz, FIG. 24 clearly indicates that the bandwidth at the mixer output is double the bandwidths at the inputs. It is readily understood by one of ordinary skill in the art that other diagnostic signal other than WiFi may be used to support this increase in bandwidth.

FIG. 24 illustrates a frequency analysis plot of the signal in which the mixer output is sampled at 40 MHz. Due to limited sampling frequency, FFT cannot show frequency more than 20 MHz. As evidenced in FIG. 24, the signal contains non-zero frequency components up to 20 MHz. One of the properties of FFT is that for a real signal, FFT components at frequencies more than half of the sampling frequency are simply reflections of components at lower frequencies. As seen in FIG. 24, FFT components at frequencies more than 20 MHz are reflections of low frequency components. For example, energy at 30 MHz is equal to that at (40−30)=10 MHz, energy at 35 MHz is equal to that at (40−35)=5 MHz, and so on. Thus, although FIG. 24 shows non-zero values for frequencies 0 to 40 MHz, energies only at frequencies 0 to 20 MHz can be estimated from this figure. In contrast, if the $I_{LO}$ input of the mixer is connected to a center frequency pure tone, both in-phase (I) and out-of-phase (Q) components contain non-zero frequency components only up to 11 MHz. In the pure tone case, the signal drops significantly after 8.3 MHz. The drop at around 8.3 MHz, instead of 11 MHz, is due to guard bands. Thus, a comparison of these empirical results indicates that the frequency at the mixer output is double of the baseband bandwidth for the input configuration shown in FIG. 22.

Therefore, in order to receive the mixer output signal intact, bandpass filters for both in-phase (I) and out-of-phase (Q) components are configured to have a minimum bandwidth of 22 MHz, having each component centered near the center frequency. Here, where $I_{LO}$ is fed with a WiFi TX signal, each of I and Q has 22 MHz bandwidth. In the normal case, that is where input to $I_{LO}$ is pure tone, each of I and Q outputs has a bandwidth of 11 MHz. In practice, two 11 MHz bandpass filters may be implemented, one for the in-phase component and the other for the out-of-phase component.

Next, a novel method of extracting and enhancing pertinent physiological information from a reflected wireless signal is provided using statistical integration methods. The tasks of extracting and enhancing pertinent physiological information from a reflected wireless signal using statistical integration methods are performed by DSP 260 of FIG. 2. In this approach, a portion of a diagnostic transmitted signal such as WiFi, for example, is reflected from different body organs of the patient in test. When the reflected signal is received and fed to the mixer 2201 as the $I_s$ input along with the original TX signal as the $I_{LO}$ input, the mixer output signal 2203 generally depends on following three parameters.

P1. Product of amplitudes of $I_s$ and $I_{LO}$.

P2. Phase difference between $I_s$ and $I_{LO}$ inputs due to difference in effective path lengths for $I_s$ and $I_{LO}$ inputs from TX antenna to the mixer. While the fixed path from TX to $I_{LO}$ comprises mainly of PCB traces, the path from TX to $I_s$ incorporates air and human tissues.

P3. Phase difference between $I_s$ and $I_{LO}$ inputs due to Doppler Effect of heart, lung and other body parts in motion. Frequency of the $I_s$ signal may be instantaneously changed due to the Doppler Effect. These frequency shifts, integrated over time, contribute to phase difference.

Each parameter has certain characteristics tied to a function of the input signals. Parameter P1 is the product of the amplitudes of $I_s$ and $I_{LO}$. The signal $I_{LO}$ is the WiFi TX signal which is basically a carrier signal (pure tone) modulated by baseband signal. Although the carrier signal has constant amplitude, the modulated signal $I_{LO}$ amplitude varies at the baseband frequency. Again, the signal $I_s$ is basically $I_{LO}$ further modulated by medium and moving objects in the propagation path. Therefore, the parameter P1 varies at the baseband frequency.

The second parameter (P2) can be assumed nearly constant for a particular setup. In the present context, the relevant part of the setup consists of the RF propagation path $\Phi_{LO}$ between the WiFi TX and $I_{LO}$ and the RF propagation path $\Phi_S$ between WiFi TX and $I_S$. Parameter P2 is the phase difference between inputs at $I_s$ and $I_{LO}$ ports. $\Phi_{LO}$ involves RF shielded wires and PCB traces and is therefore nearly constant. The overall path length of $\Phi_S$ is also nearly constant if the semi-periodic path difference due movements of vital organs is not considered (movements of vital organs are taken into consideration in parameter P3). Therefore parameter P2 is nearly constant so long as the pendant is not displaced from the chest. The third parameter is semi-periodic at very low frequencies (e.g., near 1.2 Hz for heart movement and 0.3 Hz for lung movement). Sampling of the mixer output signal 2203 may be performed at a high frequency (e.g. 40 MHz) and integrated over sufficiently large number of samples (e.g. 80,000 samples) so that the high frequency fluctuation in mixer output signal 2203 due to the first parameter (P1) is reduced, and edge signals for the third parameter (P3) attributed to the slow varying pattern due to third parameter (P3) are increased, resulting in improved detection by the DSP module 260. The detection is performed by the DSP 260. As the input to DSP 260 is improved because of integration over a large number of samples, the output of the DSP 260 is also enhanced.

Using this method, two mixers in quadrature phase relationship are used. Although the in-phase (I) or out-of-phase (Q) outputs of the mixer 2201 may be integrated directly as an attempt to isolate the third parameter (P3), a problem arises as explained below.

The I mixer output, for example, can be given by $$o_I = A_s A_{LO} \cos(\Delta\phi) \qquad (7)$$

where, $\Delta\phi$ is the phase difference between the $I_s$ and $I_{LO}$ inputs. The cosine function increases with increase in $\Delta\phi$ for some ranges of $\Delta\phi$, while it decreases with increase in $\Delta\phi$ for other ranges as follows.

$$0 \le \Delta\varphi \le \frac{\pi}{2}:$$

$\cos(\Delta\phi)$ decreases with increase in $\Delta\phi$.

$$\frac{\pi}{2} \le \Delta\varphi \le \pi:$$

$\cos(\Delta\phi)$ decreases with increase in $\Delta\phi$.

$$\pi \le \Delta\varphi \le \frac{3\pi}{2}:$$

$\cos(\Delta\phi)$ increases with increase in $\Delta\phi$.

$$\frac{3\pi}{2} \le \Delta\varphi \le 2\pi:$$

$\cos(\Delta\phi)$ increases with increase in $\Delta\phi$.

Thus for the same velocity of heart or lung, there may be increase or decrease in mixer output depending on the range of $\Delta\phi$. For example, when the lung is expanding, mixer output may increase or decrease depending on the distance of the lung surface. More importantly, as WiFi baseband signal changes fast from symbol to symbol, range of $\Delta\phi$ switches from quadrant to quadrant because of path difference between the mixer inputs. To see the effect of this fast switching, let us denote $\cos(\Delta\phi)$ when the moving object is at its neutral position as $\cos(\Delta\phi^{(0)})$ and that when the moving object is at position x(t) as $\cos(\Delta\phi^{(x)})$. The polarity of deviation, $d_x = \cos(\Delta\phi^{(x)}) - \cos(\Delta\phi^{(0)})$, toggles very fast, because of the high frequency of the baseband signal. Therefore, if we integrate a large number of samples, the integrated value of $d_x$ due to Doppler Effect will be a random number close to zero, resulting in loss of poor detection of the P3 parameter.

This problem can be solved, if the I and Q mixer output 2203 pair are first converted from Cartesian coordinate to polar coordinate ($(R, \phi)$) and integration is performed over $\phi$, defining deviation in $\phi$ as $d_\phi = \Delta\phi^{(x)} - \Delta\phi^{(0)}$. Although $\phi$ may vary from quadrant to quadrant during fast change of baseband signal, the deviation $d_\phi$ persistently increases when the moving object gets closer to the sensor. Similarly, $d_\phi$ persistently decreases when the object gets away from the sensor. Thus when integration is performed over $\phi$, the effect of frequent varying of $\phi$ from one quadrant to another is made smooth, while the persistent contribution of Doppler Effect, $d_\phi$ are enhanced, and thus improving signal detection associated with the patient's heart, lung and other body parts in motion.

Although the embodiment presented hereinabove is implemented in a medical application, the system 2200 and method for the detection of slow moving objects may be applied to other applications. Some of these applications include theft prevention through detection of thief movement, window flip detection, etc.

In another embodiment, the system 2200 may operate with the transmitted diagnostic signal supplied by an external RF source which is not provided by system 100 or system 2200. Ambient RF energy sources transmitted from public broadcasting wireless stations such as WiFi hotspots, cellular towers, satellites, or public RF transmission stations may be used as input signals to the system 2200, where the Doppler effect from reflected objects are measured directly. Publicly broadcasted wireless signals received by the system 2200 include but are not limited to WiFi, WiMAX, GPS, and OFDM. By eliminating the diagnostic transmitter portion of the system, a compact passive physiological monitoring device may be constructed at a lower cost.

Although the invention has been described in the context of a human patient, the inventive concepts described herein can be used on any type of living subject including animals. For example, the inventive concepts can be implemented in veterinarian applications where medical information is sought for animals such as dogs and cats. The device 110 may implemented as part of a collar or harness worn by the animal.

In accordance with some embodiments, the various aspects described above may be implemented using computer programming or engineering techniques including computer software, firmware, hardware or any combination or subset thereof. Any resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network. In addition, one of ordinary skill in the art of computer science will be able to combine the software created as described with appropriate general purpose or special purpose computer hardware, Personal Digital Assistant (PDA) hardware, cellular telephone hardware or other electronic hardware to create a computer system or computer sub-system embodying the method of the invention. One of ordinary skill in the art will understand that the various embodiments can also be implemented on circuitry, which, as defined herein, can be any combination of general purpose hardware, software, firmware, and/or special purpose hardware, including, but not limited to, a central processing unit, FPGA, ASIC or other known devices.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein.

The invention claimed is:

1. A method for non-invasive physiology monitoring of a living subject, the method implemented on a physiology monitoring device and comprising the steps of:
    acquiring, at the physiology monitoring device, a first modulated signal associated with an IEEE 802.11(x) orthogonal frequency-division multiplexing (OFDM) communications protocol, wherein the first modulated signal is generated by a source other than the physiology monitoring device and has passed through tissue of the living subject,
    combining, at the physiology monitoring device, the first modulated signal with itself to form a combined signal, and
    processing, at the physiology monitoring device, the combined signal to monitor a physiological function of an organ of the living subject.

2. The method of claim 1, wherein the organ is a moving organ and the second modulated signal comprises the first modulated signal having undergone a Doppler effect due to the moving organ of the living subject.

3. The method of claim 1, wherein the combined signal comprises a bandwidth that is substantially double of the first modulated signal.

4. The method of claim 1, wherein the physiological function is selected from the group consisting of: heart rate; respiratory or pulmonary rate; ventricular contraction; ventricular relaxation; atrial contraction; atrial relaxation; arrhythmia; and a combination thereof.

5. The method of claim 1, further comprising the step of detecting, at the physiology monitoring device, movement of the living subject.

6. The method of claim 5, wherein the movement comprises a fall.

7. The method of claim 5, further comprising the step of recording, at the physiology monitoring device, the monitored physiological function upon detection of the movement.

8. The method of claim 1, wherein the step of processing comprises extracting deviations from randomness in the combined signal.

9. A non-invasive system for physiology monitoring of a living subject comprising:
    a mixer for receiving a modulated signal associated with an IEEE 802.11(x) orthogonal frequency-division multiplexing (OFDM) communications protocol from a remote source and having passed through tissue of the living subject, wherein an output signal is generated by the mixer, wherein the output signal comprises the modulated signal combined with itself,
    a filter coupled to the mixer for receiving the output signal, and
    circuitry to determine and monitor a physiological function of an organ of the living subject, wherein the circuitry processes the output signal.

10. The system for physiology monitoring of claim 9, wherein the output signal comprises a bandwidth that is substantially double of the modulated signal.

11. The system for physiology monitoring of claim 9, wherein the modulated signal is attributed to a Doppler effect reflected from the organ of the living subject.

12. The system for physiology monitoring of claim 9, wherein the circuitry comprises a digital signal processing unit to measure, convert and analyze the output signal for determining and monitoring a physiological function of an organ of the living subject.

13. The system for physiology monitoring of claim 9, wherein the remote source is an IEEE 802.11(x) access point.

14. The system for physiology monitoring of claim 9, wherein the filter comprises a low pass filter or a bandpass filter.

15. The system of claim 9, wherein the circuitry processes the output signal to extract deviations from randomness in the output signal.

* * * * *